United States Patent
Tchaga et al.

(10) Patent No.: US 7,176,298 B2
(45) Date of Patent: Feb. 13, 2007

(54) POLYNUCLEOTIDES ENCODING METAL ION AFFINITY PEPTIDES AND RELATED PRODUCTS

(75) Inventors: Grigoriy S. Tchaga, Newark, CA (US); George G. Jokhadze, Mountain View, CA (US)

(73) Assignee: Clontech Laboratories, Inc., Mountain View, CA (US)

( * ) Notice: Subject to any disclaimer, the term of this patent is extended or adjusted under 35 U.S.C. 154(b) by 103 days.

(21) Appl. No.: 09/858,332

(22) Filed: May 15, 2001

(65) Prior Publication Data

US 2002/0164718 A1 Nov. 7, 2002

Related U.S. Application Data

(63) Continuation-in-part of application No. 09/404,017, filed on Sep. 23, 1999, now abandoned.

(60) Provisional application No. 60/101,867, filed on Sep. 25, 1998.

(51) Int. Cl.
C07H 21/02 (2006.01)
C07H 21/04 (2006.01)
C12N 15/63 (2006.01)
C12N 1/20 (2006.01)
C12N 15/00 (2006.01)

(52) U.S. Cl. .................. 536/23.4; 536/23.1; 435/320.1; 435/252.3; 435/252.33; 435/325; 435/348

(58) Field of Classification Search .............. 536/23.1, 536/23.2; 435/320.1, 252.3, 354.11, 325, 435/419
See application file for complete search history.

(56) References Cited

U.S. PATENT DOCUMENTS

| | | | |
|---|---|---|---|
| 4,569,794 A | 2/1986 | Smith et al. | |
| 5,284,933 A | 2/1994 | Dobeli et al. | |
| 5,310,663 A | 5/1994 | Dobeli et al. | |
| 5,439,829 A | 8/1995 | Anderson et al. | |
| 5,498,538 A | 3/1996 | Kay et al. | |
| 5,594,115 A | 1/1997 | Sharma | |
| 5,670,483 A * | 9/1997 | Zhang et al. | 514/14 |
| 2003/0079237 A1 * | 4/2003 | Sato | 800/8 |

OTHER PUBLICATIONS

Chaga et al. Natural poly-histidine affinity tag for purification of recombinant proteins on cobalt(II)-carboxymethylasparate crosslinked agarose. J. Chromat. (1999) 864:247-256.*

Giraldo et al. Characterization of a *Plasmodium chabaudi* gene endcoding a protein with glutamate-rich tandem repeats. Parasitology Research (1999) 85:41-46.*

GenBank Accession No. AF019972. *Plasmodium chabaudi* NE-rich protein gene, Mar. 23, 1999.*

Chaga et al. Immobilized metal ion affinity chromatography of Co2+-carboxymethylaspartate-agarose Superflow, as demonstrated by one-step purification of lactate dehydrogenase from chicken breast muscle. Biotechnol. Appl. Biochem. (1999) 29:19-24.*

CLONTECHniques. PROTet 6xHN Bacterial Expression System. Oct. 1999. pp. 23-24.*

CLONTECHniques. HAT Protein Expression & Purification System. Jul. 1998.*

Ford et al. (1991) "Fusion Tails for the recovery and purification of recombinant proteins." *Protein Expression and Purification*, vol. 2:95-107.

Hirota et al. (1990) "Nucleotide and Deduced Amino Acid Sequences of Chicken Lactate Dehydrogenase-A." *Nucleic Acids Research*, vol. 18(21):6432.

Leuthardt et al. (1993) "Cloning, expression and purification of a recombinant poly-histidine-linked HIV-1 protease." *FEBS Letters*, vol. 326(1-3):275-280.

Ljungquist et al. (1989) "Immobilization and Affinity Purification of Recombinant Proteins Using Histidine Peptide Fusions." *Eur. J. Biochem.*, vol. 186:563-569.

(Continued)

*Primary Examiner*—Sheridan Swope
(74) *Attorney, Agent, or Firm*—Bret E. Field; David C. Scherer; Bozicevic, Field & Francis LLP

(57) ABSTRACT

The present invention provides metal ion affinity peptides, fusion proteins comprising metal ion affinity peptides, and polynucleotides encoding the fusion proteins. A feature of the subject invention is that the metal ion affinity peptide has a formula selected from the group consisting of: formula 1: $(His-X_1-X_2)_{n1}-(His-X_3-X_4-X_5)_{n2}-(His-X_6)_{n3}$, wherein each of $X_1$ and $X_2$ is independently an amino acid with an aliphatic or an amide side chain, each of $X_3$, $X_4$, $X_5$ is independently an amino acid with a basic side chain (except His) or an acidic side chain, each $X_6$ is an amino acid with an aliphatic or an amide side chain, n1 and n2 are each independently 1–3, and n3 is 1–5; formula 2: $(His-Asn)_n$, where n=3 to 10; and formula 3: $(His-X_1-X_2)_n$, wherein each of $X_1$ and $X_2$ is an amino acid having an acidic side chain, and n=3 to 10. The invention further provides recombinant vectors comprising subject polynucleotides, and host cells comprising the recombinant vectors. The invention further provides methods and kits for purifying a fusion protein comprising a metal ion affinity peptide.

18 Claims, 8 Drawing Sheets

OTHER PUBLICATIONS

Figure 1:
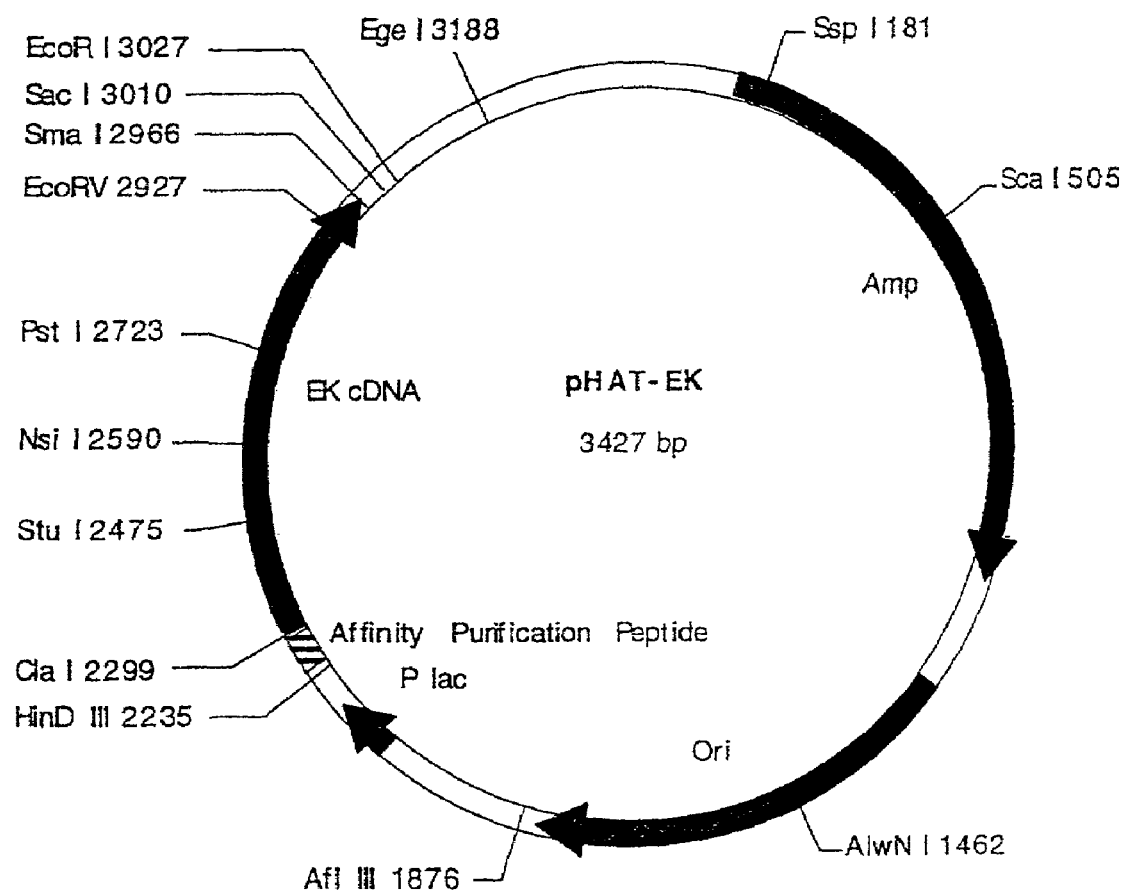

Moser et al. (1994) "Recombinant Expression and antigenic properties of a 32-kilodalton extracellular alkaline protease, representing a possible virulence factor from *Aspergillus fumigatus*." Infectious Immunology, vol. 62(3):936-942.

Nakajima et al. (1989) "Molecular aspect of myogenic hyperuricemia of human muscle phosphofructokinase cDNA." *Advances in Experimental Medicine and Biology*, vol. 253A:485-491.

Nilsson et al. (1997) "Affinity Fusion strategies for Detection, Purification, and Immobilization of recombinant proteins." *Protein Expression and Purification*, vol. 11:1-16.

Smith et al. (1988) "Chelating Peptide-Immobilized Metal Ion affinity Chromatography." *The Journal of Biological Chemistry*, vol. 263(15):7211-7215.

Stader et al. (1990) "Engineering *Escherichia coli* to Secrete Heterologous Gene Products." *Methods in Enzymology: Gene Expression Technology*, vol. 185:166-185.

Walker et al. (1994) "Efficient and Rapid Affinity Purification of Proteins using 'Recombinant Fusion Proteases." *Biotechnology*, vol. 12(6):601-605.

Germino et al. (1983) "Use of gene fusions and protein-protein interaction in the isolation of a biologically active regulatory protein: the replication initiator protein of plasmid R6K." *Proc. Natl. Acad. Sci.* USA, vol. 80:6848-52.

Itakura et al. (1977) "Expression in *Escherichia coli* of a chemically synthesized gene for the hormone somatostatin." *Science*, vol. 198:1056-63.

Nilsson et al. (1985) "Efficient secretion and purification of human insulin-like growth factor I with a gene fusion vector in Staphylococci." *Nucleic Acids Res.*, vol. 13:1151-62.

Smith et al. (1984) "Chemical synthesis and cloning of a poly(arginine)-coding gene fragment designed to aid polypeptide purification." *Gene*, vol. 32:321-27.

* cited by examiner

```
1/1                                           31/11
GAC GAA AGG GCC TCG TGA TAC GCC TAT TTT      TAT AGG TTA ATG TCA TGA TAA TAA TGG TTT
61/21                                         91/31
CTT AGA CGT CAG GTG GCA CTT TTC GGG GAA      ATG TGC GCG GAA CCC CTA TTT GTT TAT TTT
121/41                                        151/51
TCT AAA TAC ATT CAA ATA TGT ATC CGC TCA      TGA GAC AAT AAC CCT GAT AAA TGC TTC AAT
181/61                                        211/71
AAT ATT GAA AAA GGA AGA GTA TGA GTA TTC      AAC ATT TCC GTG TCG CCC TTA TTC CCT TTT
241/81                                        271/91
TTG CGG CAT TTT GCC TTC CTG TTT TTG CTC      ACC CAG AAA CGC TGG TGA AAG TAA AAG ATG
301/101                                       331/111
CTG AAG ATC AGT TGG GTG CAC GAG TGG GTT      ACA TCG AAC TGG ATC TCA ACA GCG GTA AGA
361/121                                       391/131
TCC TTG AGA GTT TTC GCC CCG AAG AAC GTT      TTC AAA TGA TGA GCA CTT TTA AAG TTC TGC
421/141                                       451/151
TAT GTG GCG CGG TAT TAT CCC GTA TTG ACG      CCG GGC AAG AGC AAC TCG GTC GCC GCA TAC
481/161                                       511/171
ACT ATT CTC AGA ATG ACT TGG TTG AGT ACT      CAC CAG TCA CAG AAA AGC ATC TTA CGG ATG
541/181                                       571/191
GCA TGA CAG TAA GAG AAT TAT GCA GTG CTG      CCA TAA CCA TGA GTG ATA ACA CTG CGG CCA
601/201                                       631/211
ACT TAC TTC TGA CAA CGA TCG GAG GAC CGA      AGG AGC TAA CCG CTT TTT TGC ACA ACA TGG
661/221                                       691/231
GGG ATC ATG TAA CTC GCC TTG ATC GTT GGG      AAC CGG AGC TGA ATG AAG CCA TAC CAA ACG
721/241                                       751/251
ACG AGC GTG ACA CCA CGA TGC CTG TAG CAA      TGG CAA CAA CGT TGC GCA AAC TAT TAA CTG
781/261                                       811/271
GCG AAC TAC TTA CTC TAG CTT CCC GGC AAC      AAT TAA TAG ACT GGA TGG AGG CGG ATA AAG
841/281                                       871/291
TTG CAG GAC CAC TTC TGC GCT CGG CCC TTC      CGG CTG GCT GGT TTA TTG CTG ATA AAT CTG
901/301                                       931/311
GAG CCG GTG AGC GTG GGT CTC GCG GTA TCA      TTG CAG CAC TGG GGC CAG ATG GTA AGC CCT
961/321                                       991/331
CCC GTA TCG TAG TTA TCT ACA CGA CGG GGA      GTC AGG CAA CTA TGG ATG AAC GAA ATA GAC
1021/341                                      1051/351
AGA TCG CTG AGA TAG GTG CCT CAC TGA TTA      AGC ATT GGT AAC TGT CAG ACC AAG TTT ACT
1081/361                                      1111/371
CAT ATA TAC TTT AGA TTG ATT AAA AAC TTC      ATT TTT AAT TTA AAA GGA TCT AGG TGA AGA
1141/381                                      1171/391
TCC TTT TTG ATA ATC TCA TGA CCA AAA TCC      CTT AAC GTG AGT TTT CGT TCC ACT GAG CGT
1201/401                                      1231/411
CAG ACC CCG TAG AAA AGA TCA AAG GAT CTT      CTT GAG ATC CTT TTT TTC TGC GCG TAA TCT
1261/421                                      1291/431
GCT GCT TGC AAA CAA AAA AAC CAC CGC TAC      CAG CGG TGG TTT GTT TGC CGG ATC AAG AGC
1321/441                                      1351/451
TAC CAA CTC TTT TTC CGA AGG TAA CTG GCT      TCA GCA GAG CGC AGA TAC CAA ATA CTG TCC
1381/461                                      1411/471
TTC TAG TGT AGC CGT AGT TAG GCC ACC ACT      TCA AGA ACT CTG TAG CAC CGC CTA CAT ACC
1441/481                                      1471/491
TCG CTC TGC TAA TCC TGT TAC CAG TGG CTG      CTG CCA GTG GCG ATA AGT CGT GTC TTA CCG
1501/501                                      1531/511
GGT TGG ACT CAA GAC GAT AGT TAC CGG ATA      AGG CGC AGC GGT CGG GCT GAA CGG GGG GTT
1561/521                                      1591/531
CGT GCA CAC AGC CCA GCT TGG AGC GAA CGA      CCT ACA CCG AAC TGA GAT ACC TAC AGC GTG
1621/541                                      1651/551
AGC TAT GAG AAA GCG CCA CGC TTC CCG AAG      GGA GAA AGG CGG ACA GGT ATC CGG TAA GCG
```

FIGURE 2A

```
1681/561                                    1711/571
GCA GGG TCG GAA CAG GAG AGC GCA CGA GGG AGC TTC CAG GGG GAA ACG CCT GGT ATC TTT
1741/581                                    1771/591
ATA GTC CTG TCG GGT TTC GCC ACC TCT GAC TTG AGC GTC GAT TTT TGT GAT GCT CGT CAG
1801/601                                    1831/611
GGG GGC GGA GCC TAT GGA AAA ACG CCA GCA ACG CGG CCT TTT TAC GGT TCC TGG CCT TTT
1861/621                                    1891/631
GCT GGC CTT TTG CTC ACA TGT TCT TTC CTG CGT TAT CCC CTG ATT CTG TGG ATA ACC GTA
1921/641                                    1951/651
TTA CCG CCT TTG AGT GAG CTG ATA CCG CTC GCC GCA GCC GAA CGA CCG AGC GCA GCG AGT
leu pro pro leu ser glu leu ile pro leu ala ala ala glu arg pro ser ala ala ser
1981/661                                    2011/671
CAG TGA GCG AGG AAG CGG AAG AGC GCC CAA TAC GCA AAC CGC CTC TCC CCG CGC GTT GGC
gln OPA ala arg lys arg lys ser ala gln tyr ala asn arg leu ser pro arg val gly
2041/681                                    2071/691
CGA TTC ATT AAT GCA GCT GGC ACG ACA GGT TTC CCG ACT GGA AAG CGG GCA GTG AGC GCA
arg phe ile asn ala ala gly thr thr gly phe pro thr gly lys arg ala val ser ala
2101/701                                    2131/711
ACG CAA TTA ATG TGA GTT AGC TCA CTC ATT AGG CAC CCC AGG CTT TAC ACT TTA TGC TTC
2161/721                                    2191/731
CGG CTC GTA TGT TGT GTG GAA TTG TGA GCG GAT AAC AAT TTC ACA CAG GAA ACA GCT atg
                                                                             met
2221/741                                    2251/751
acc atg att acg cca agc ttg AAG GAT CAT CTC ATC ACC AAT GTC CAC AAA GAG GAG CAC
thr met ile thr pro ser leu lys asp his leu ile his asn val his lys glu glu his
2281/761                                    2311/771
GCT CAT GCC CAC AAC AAG ATC GAT att gtc gga gga agt gac tcc aga gaa gga gcc tgg
ala his ala his asn lys ile asp ile val gly gly ser asp ser arg glu gly ala trp
2341/781                                    2371/791
cct tgg gtc gtt gct ctg tat ttc gac gat caa cag gtc tgc gga gct tct ctg gtg agc
pro trp val val ala leu tyr phe asp asp gln gln val cys gly ala ser leu val ser
2401/801                                    2431/811
agg gat tgg ctg gtg tcg gcc gcc cac tgc gtg tac ggg aga aat atg gag ccg tct aag
arg asp trp leu val ser ala ala his cys val tyr gly arg asn met glu pro ser lys
2461/821                                    2491/831
tgg aaa gca gtg cta ggc ctg cat atg gca tca aat ctg act tct cct cag ata gaa act
trp lys ala val leu gly leu his met ala ser asn leu thr ser pro gln ile glu thr
2521/841                                    2551/851
agg ttg att gac caa att gtc ata aac cca cac tac aat aaa cgg aga aag aac aat gac
arg leu ile asp gln ile val ile asn pro his tyr asn lys arg arg lys asn asn asp
2581/861                                    2611/871
att gcc atg atg cat ctt gaa atg aaa gtg aac tac aca gat tat ata cag cct att tgt
ile ala met met his leu glu met lys val asn tyr thr asp tyr ile gln pro ile cys
2641/881                                    2671/891
tta cca gaa gaa aat caa gtt ttt ccc cca gga aga att tgt tct att gct ggc tgg ggg
leu pro glu glu asn gln val phe pro pro gly arg ile cys ser ile ala gly trp gly
2701/901                                    2731/911
gca ctt ata tat caa ggt tct act gca gac gta ctg caa gaa gct gac gtt ccc ctt cta
ala leu ile tyr gln gly ser thr ala asp val leu gln glu ala asp val pro leu leu
2761/921                                    2791/931
tca aat gag aaa tgt caa caa cag atg cca gaa tat aac att acg gaa aat atg gtg tgt
ser asn glu lys cys gln gln gln met pro glu tyr asn ile thr glu asn met val cys
2821/941                                    2851/951
gca ggc tat gaa gca gga ggg gta gat tct tgt cag ggg gat tca ggc gga cca ctc atg
ala gly tyr glu ala gly gly val asp ser cys gln gly asp ser gly gly pro leu met
2881/961                                    2911/971
tgc caa gaa aac aac aga tgg ctc ctg gct ggc gtg acg tca ttt gga tat caa tgt gca
cys gln glu asn asn arg trp leu leu ala gly val thr ser phe gly tyr gln cys ala
2941/981                                    2971/991
ctg cct aat cgc cca ggg gtg tat gcc cgg gtc cca agg ttc aca gag tgg ata caa agt
leu pro asn arg pro gly val tyr ala arg val pro arg phe thr glu trp ile gln ser
3001/1001                                   3031/1011
ttt cta cat GAG CTC GTA ATT AGC TGA GAA TTC ACT GGC CGT CGT TTT ACA ACG TCG TGA
phe leu his glu leu val ile ser OPA glu phe thr gly arg arg phe thr thr ser OPA
```

FIGURE 2B

```
3061/1021                              3091/1031
CTG GGA AAA CCC TGG CGT TAC CCA ACT TAA TCG CCT TGC AGC ACA TCC CCC TTT CGC CAG
3121/1041                              3151/1051
CTG GCG TAA TAG CGA AGA GGC CCG CAC CGA TCG CCC TTC CCA ACA GTT GCG CAG CCT GAA
3181/1061                              3211/1071
TGG CGA ATG GCG CCT GAT GCG GTA TTT TCT CCT TAC GCA TCT GTG CGG TAT TTC ACA CCG
3241/1081                              3271/1091
CAT ATG GTG CAC TCT CAG TAC AAT CTG CTC TGA TGC CGC ATA GTT AAG CCA GCC CCG ACA
3301/1101                              3331/1111
CCC GCC AAC ACC CGC TGA CGC GCC CTG ACG GGC TTG TCT GCT CCC GGC ATC CGC TTA CAG
3361/1121                              3391/1131
ACA AGC TGT GAC CGT CTC CGG GAG CTG CAT GTG TCA GAG GTT TTC ACC GTC ATC ACC GAA
3421/1141
ACG CGC
```

FIGURE 2C

Insert 1

```
1/1                                              31/11
CAT CTC ATC CAC AAT GTC CAC AAA GAG GAG CAC GCT CAT GCC CAC AAC (SEQ ID NO:16)
his leu ile his asn val his lys glu glu his ala his ala his asn (SEQ ID NO:01)
```

Insert 2

```
1/1                                              31/11
CAT AAC CAT AAC CAT AAC CAT AAC CAT AAC CAT AAC (SEQ ID NO:17)
his asn his asn his asn his asn his asn his asn (SEQ ID NO:15)
```

Insert 3

```
1/1                                              31/11
CAT GAT GAT CAT GAT GAT CAT GAT GAT CAT GAT GAT CAT GAT GAT (SEQ ID NO:18)
his asp asp his asp asp his asp asp his asp asp his asp asp (SEQ ID NO:02)
```

Insert 4

```
1/1                                              31/11
CAT GAG GAG CAT GAG GAG CAT GAG GAG CAT GAG GAG CAT GAG GAG (SEQ ID NO:19)
his glu glu his glu glu his glu glu his glu glu his glu glu (SEQ ID NO:03)
```

Insert 5

```
1/1                                              31/11
CAT GAT GAG CAT GAT GAG CAT GAG AAC CAT GAG AAC CAT GAG GAT CAT GAG GAT (SEQ ID NO:20)
his asp glu his asp glu his glu asn his glu asn his glu asp his glu asp (SEQ ID NO:04)
```

FIGURE 3

Sample: HN6-DHFR expressing E.coli cells (0.54 g) extracted in 4.35 mL of 50 mM sodium phosphate; 0.3 M NaCl; 10 mM imidazole pH 7.0
Column: 3.5 x 1 cm.i.d. Co(II)-carboxymethylaspartate-agarose (Superflow) equilibrated with the extraction buffer
Flow rate: 1 mL per minute (1.25 cm per minute)
Peak I - non adsorbed material
Peak II - HAT-DHFR

SEQUENCE LISTING

```
<160> NUMBER OF SEQ ID NOS: 33

<210> SEQ ID NO 1
<211> LENGTH: 16
<212> TYPE: PRT
<213> ORGANISM: Artificial Sequence
<220> FEATURE:
<223> OTHER INFORMATION: affinity peptide

<400> SEQUENCE: 1

His Leu Ile His Asn Val His Lys Glu Glu His Ala His Ala His Asn
1               5                   10                  15

<210> SEQ ID NO 2
<211> LENGTH: 18
<212> TYPE: PRT
<213> ORGANISM: Artificial Sequence
<220> FEATURE:
<223> OTHER INFORMATION: affinity peptide

<400> SEQUENCE: 2

His Asp Asp His Asp Asp His Asp Asp His Asp Asp His Asp Asp His
```

```
                1               5              10              15
Asp Asp

<210> SEQ ID NO 3
<211> LENGTH: 18
<212> TYPE: PRT
<213> ORGANISM: Artificial Sequence
<220> FEATURE:
<223> OTHER INFORMATION: affinity peptide

<400> SEQUENCE: 3

His Glu Glu His Glu Glu His Glu Glu His Glu Glu His Glu Glu His
  1               5              10              15

Glu Glu

<210> SEQ ID NO 4
<211> LENGTH: 18
<212> TYPE: PRT
<213> ORGANISM: Artificial Sequence
<220> FEATURE:
<223> OTHER INFORMATION: affinity peptide

<400> SEQUENCE: 4

His Asp Glu His Asp Glu His Glu Asn His Glu Asn His Glu Asp His
  1               5              10              15

Glu Asp

<210> SEQ ID NO 5
<211> LENGTH: 18
<212> TYPE: PRT
<213> ORGANISM: Artificial Sequence
<220> FEATURE:
<223> OTHER INFORMATION: affinity peptide

<400> SEQUENCE: 5

His Glu Asp His Glu Asp His Glu Asp His Glu Asp His Glu Asp His
  1               5              10              15

Glu Asp

<210> SEQ ID NO 6
<211> LENGTH: 5
<212> TYPE: PRT
<213> ORGANISM: Artificial Sequence
<220> FEATURE:
<223> OTHER INFORMATION: affinity peptide

<400> SEQUENCE: 6

Asp Asp Asp Asp Lys
  1               5

<210> SEQ ID NO 7
<211> LENGTH: 4
<212> TYPE: PRT
<213> ORGANISM: Artificial Sequence
<220> FEATURE:
<223> OTHER INFORMATION: factor Xa cleavage site

<400> SEQUENCE: 7

Ile Glu Gly Arg
  1

<210> SEQ ID NO 8
<211> LENGTH: 6
<212> TYPE: PRT
```

```
<213> ORGANISM: Artificial Sequence
<220> FEATURE:
<223> OTHER INFORMATION: thrombin cleavage site

<400> SEQUENCE: 8

Leu Val Pro Arg Gly Ser
 1               5

<210> SEQ ID NO 9
<211> LENGTH: 8
<212> TYPE: PRT
<213> ORGANISM: Artificial Sequence
<220> FEATURE:
<223> OTHER INFORMATION: renin cleavage site

<400> SEQUENCE: 9

His Pro Phe His Leu Val Ile His
 1               5

<210> SEQ ID NO 10
<211> LENGTH: 10
<212> TYPE: PRT
<213> ORGANISM: Artificial Sequence
<220> FEATURE:
<223> OTHER INFORMATION: an immunological tag

<400> SEQUENCE: 10

Cys Tyr Pro Tyr Asp Val Pro Asp Tyr Ala
 1               5                  10

<210> SEQ ID NO 11
<211> LENGTH: 8
<212> TYPE: PRT
<213> ORGANISM: Artificial Sequence
<220> FEATURE:
<223> OTHER INFORMATION: an immunological tag

<400> SEQUENCE: 11

Asp Tyr Lys Asp Asp Asp Asp Lys
 1               5

<210> SEQ ID NO 12
<211> LENGTH: 11
<212> TYPE: PRT
<213> ORGANISM: Artificial Sequence
<220> FEATURE:
<223> OTHER INFORMATION: an immunological tag

<400> SEQUENCE: 12

Cys Glu Gln Lys Leu Ile Ser Glu Glu Asp Leu
 1               5                  10

<210> SEQ ID NO 13
<211> LENGTH: 3426
<212> TYPE: DNA
<213> ORGANISM: Artificial Sequence
<220> FEATURE:
<223> OTHER INFORMATION: DNA sequence of vector containing cDNA of
      recombinant enterokinase

<400> SEQUENCE: 13
gacgaaaggg cctcgtgata cgcctatttt tataggttaa tgtcatgata ataatggttt    60
cttagacgtc aggtggcact tttcggggaa atgtgcgcgg aaccccctatt tgtttatttt   120 tctaaataca ttcaaatatg tatccgctca tgagacaata accctgataa atgcttcaat   180
aatattgaaa aaggaagagt atgagtattc aacatttccg tgtcgccctt attccctttt   240
```

-continued

```
ttgcggcatt ttgccttcct gttttttgctc acccagaaac gctggtgaaa gtaaaagatg      300
ctgaagatca gttgggtgca cgagtgggtt acatcgaact ggatctcaac agcggtaaga      360
tccttgagag ttttcgcccc gaagaacgtt ttccaatgat gagcactttt aaagttctgc      420
tatgtggcgc ggtattatcc cgtattgacg ccgggcaaga gcaactcggt cgccgcatac      480
actattctca gaatgacttg gttgagtact caccagtcac agaaaagcat cttacggatg      540
gcatgacagt aagagaatta tgcagtgctg ccataaccat gagtgataac actgcggcca      600
acttacttct gacaacgatc ggaggaccga aggagctaac cgctttttg cacaacatgg      660 gggatcatgt aactcgcctt gatcgttggg aaccggagct gaatgaagcc ataccaaacg      720
acgagcgtga caccacgatg cctgtagcaa tggcaacaac gttgcgcaaa ctattaactg      780
gcgaactact tactctagct tcccggcaac aattaataga ctggatggag gcggataaag      840
ttgcaggacc acttctgcgc tcggcccttc cggctggctg gtttattgct gataaatctg      900
gagccggtga gcgtgggtct cgcggtatca ttgcagcact ggggccagat ggtaagccct      960
cccgtatcgt agttatctac acgacgggga gtcaggcaac tatggatgaa cgaaatagac     1020
agatcgctga gataggtgcc tcactgatta agcattggta actgtcagac caagtttact     1080
catatatact ttagattgat ttaaaacttc atttttaatt taaaaggatc taggtgaaga     1140 tccttttga taatctcatg accaaaatcc cttaacgtga gttttcgttc cactgagggt      1200
cagaccccgt agaaaagatc aaaggatctt cttgagatcc ttttttttctg cgcgtaatct     1260 gctgcttgca acaaaaaaa ccaccgctac cagcggtggt ttgtttgccg gatcaagagc     1320
taccaactct ttttccgaag gtaactggct tcagcagagc gcagatacca atactgtcc      1380 ttctagtgta gccgtagtta ggccaccact tcaagaactc tgtagcaccg cctacatacc     1440
tcgctctgct aatcctgtta ccagtggctg ctgccagtgg cgataagtcg tgtcttaccg     1500
ggttggactc aagacgatag ttaccggata aggcgcagcg gtcgggctga acggggggtt     1560
cgtgcacaca gcccagcttg gagcgaacga cctacaccga actgagatac ctacagcgtg     1620
agctatgaga aagcgccacg cttcccgaag ggagaaaggc ggacaggtat ccggtaagcg     1680
gcagggtcgg aacaggagag cgcacgaggg agcttccagg gggaaacgcc tggtatcttt     1740
atagtcctgt cgggtttcgc cacctctgac ttgagcgtcg attttgtga tgctcgtcag     1800 gggggcggag cctatggaaa aacgccagca acgcggcctt tttacggttc ctggccttt      1860 gctggccttt tgctcacatg ttctttcctg cgttatcccc tgattctgtg ataaccgta     1920 ttaccgcctt tgagtgagct gataccgctc gccgcagccg aacgaccgag cgcagcgagt     1980
cagtgagcga ggaagcggaa gagcgcccaa tacgcaaacc gcctctcccc gcgcgttggc     2040
cgattcatta atgcagctgg cacgacaggt ttcccgactg gaaagcgggc agtgagcgca     2100
acgcaattaa tgtgagttag ctcactcatt aggcacccca ggctttacac tttatgcttc     2160
cggctcgtat gttgtgtgga attgtgagcg ataacaatt tcacacagga acagctatg     2220 accatgatta cgccaagctt gaaggatcat ctcatccaca atgtccacaa agaggagcac     2280
gctcatgccc acaacaagat cgatattgtc ggaggaagtg actccagaga aggagcctgg     2340
ccttgggtcg ttgctctgta tttcgacgat caacaggtct gcggagcttc tctggtgagc     2400
agggattggc tggtgtcggc cgcccactgc gtgtacggga gaaatatgga gccgtctaag     2460
tggaaagcag tgctaggcct gcatatggca tcaaatctga cttctcctca gatagaaact     2520
aggttgattg accaaattgt cataaaccca cactacaata aacggagaaa gaacaatgac     2580
```

-continued

```
attgccatga tgcatcttga aatgaaagtg aactacacag attatataca gcctatttgt      2640
ttaccagaag aaaatcaagt ttttccccca ggaagaattt gttctattgc tggctggggg      2700
gcacttatat atcaaggttc tactgcagac gtactgcaag aagctgacgt tccccttcta      2760
tcaaatgaga aatgtcaaca acagatgcca gaatataaca ttacggaaaa tatggtgtgt      2820
gcaggctatg aagcaggagg ggtagattct tgtcagggg attcaggcgg accactcatg       2880
tgccaagaaa acaacagatg gctcctggct ggcgtgacgt catttggata tcaatgtgca      2940
ctgcctaatc gcccaggggt gtatgcccgg gtcccaaggt tcacagagtg gatacaaagt      3000
tttctacatg agctcgtaat tagctgagaa ttcactggcc gtcgttttac aacgtcgtga      3060
ctgggaaaac cctggcgtta cccaacttaa tcgccttgca gcacatcccc ctttcgccag      3120
ctggcgtaat agcgaagagg cccgcaccga tcgcccttcc caacagttgc gcagcctgaa      3180
tggcgaatgg cgcctgatgc ggtattttct ccttacgcat ctgtgcggta tttcacaccg      3240
catatggtgc actctcagta caatctgctc tgatgccgca tagttaagcc agccccgaca      3300
cccgccaaca cccgctgacg cgccctgacg ggcttgtctg ctcccggcat ccgcttacag      3360
acaagctgtg accgtctccg ggagctgcat gtgtcagagg ttttcaccgt catcaccgaa      3420
acgcgc                                                                3426
```

<210> SEQ ID NO 14
<211> LENGTH: 269
<212> TYPE: PRT
<213> ORGANISM: Artificial Sequence
<220> FEATURE:
<223> OTHER INFORMATION: protein sequence of vector containing cDNA of recombinant enterokinase

<400> SEQUENCE: 14

```
Met Thr Met Ile Thr Pro Ser Leu Lys Asp His Leu Ile His Asn Val
 1               5                  10                  15

His Lys Glu Glu His Ala His Ala His Asn Lys Ile Asp Ile Val Gly
            20                  25                  30

Gly Ser Asp Ser Arg Glu Gly Ala Trp Pro Trp Val Val Ala Leu Tyr
        35                  40                  45

Phe Asp Asp Gln Gln Val Cys Gly Ala Ser Leu Val Ser Arg Asp Trp
    50                  55                  60

Leu Val Ser Ala Ala His Cys Val Tyr Gly Arg Asn Met Glu Pro Ser
65                  70                  75                  80

Lys Trp Lys Ala Val Leu Gly Leu His Met Ala Ser Asn Leu Thr Ser
                85                  90                  95

Pro Gln Ile Glu Thr Arg Leu Ile Asp Gln Ile Val Ile Asn Pro His
            100                 105                 110

Tyr Asn Lys Arg Arg Lys Asn Asn Asp Ile Ala Met Met His Leu Glu
        115                 120                 125

Met Lys Val Asn Tyr Thr Asp Tyr Ile Gln Pro Ile Cys Leu Pro Glu
    130                 135                 140

Glu Asn Gln Val Phe Pro Pro Gly Arg Ile Cys Ser Ile Ala Gly Trp
145                 150                 155                 160

Gly Ala Leu Ile Tyr Gln Gly Ser Thr Ala Asp Val Leu Gln Glu Ala
                165                 170                 175

Asp Val Pro Leu Leu Ser Asn Glu Lys Cys Gln Gln Gln Met Pro Glu
            180                 185                 190

Tyr Asn Ile Thr Glu Asn Met Val Cys Ala Gly Tyr Glu Ala Gly Gly
        195                 200                 205
```

```
Val Asp Ser Cys Gln Gly Asp Ser Gly Gly Pro Leu Met Cys Gln Glu
    210                 215                 220

Asn Asn Arg Trp Leu Leu Ala Gly Val Thr Ser Phe Gly Tyr Gln Cys
225                 230                 235                 240

Ala Leu Pro Asn Arg Pro Gly Val Tyr Ala Arg Val Pro Arg Phe Thr
                245                 250                 255

Glu Trp Ile Gln Ser Phe Leu His Glu Leu Val Ile Ser
            260                 265

<210> SEQ ID NO 15
<211> LENGTH: 12
<212> TYPE: PRT
<213> ORGANISM: Artificial Sequence
<220> FEATURE:
<223> OTHER INFORMATION: an amino acid sequence embodiment of the
      affinity purification site

<400> SEQUENCE: 15

His Asn His Asn His Asn His Asn His Asn His Asn
 1               5                  10

<210> SEQ ID NO 16
<211> LENGTH: 48
<212> TYPE: DNA
<213> ORGANISM: Artificial Sequence
<220> FEATURE:
<223> OTHER INFORMATION: a DNA sequence embodiment of the affinity
      purification site

<400> SEQUENCE: 16
catctcatcc acaatgtcca caaagaggag cacgctcatg cccacaac                48

<210> SEQ ID NO 17
<211> LENGTH: 36
<212> TYPE: DNA
<213> ORGANISM: Artificial Sequence
<220> FEATURE:
<223> OTHER INFORMATION: a DNA sequence embodiment of the affinity
      purification site

<400> SEQUENCE: 17
cataaccata accataacca taaccataac cataac                             36

<210> SEQ ID NO 18
<211> LENGTH: 54
<212> TYPE: DNA
<213> ORGANISM: Artificial Sequence
<220> FEATURE:
<223> OTHER INFORMATION: a DNA sequence embodiment of the affinity
      purification site

<400> SEQUENCE: 18
catgatgatc atgatgatca tgatgatcat gatgatcatg atgatcatga tgat         54

<210> SEQ ID NO 19
<211> LENGTH: 54
<212> TYPE: DNA
<213> ORGANISM: Artificial Sequence
<220> FEATURE:
<223> OTHER INFORMATION: a DNA sequence embodiment of the affinity
      purification site

<400> SEQUENCE: 19
catgaggagc atgaggagca tgaggagcat gaggagcatg aggagcatga ggag         54
```

```
<210> SEQ ID NO 20
<211> LENGTH: 54
<212> TYPE: DNA
<213> ORGANISM: Artificial Sequence
<220> FEATURE:
<223> OTHER INFORMATION: a DNA sequence embodiment of the affinity
      purification site

<400> SEQUENCE: 20
catgatgagc atgatgagca tgagaaccat gagaaccatg aggatcatga ggat          54

<210> SEQ ID NO 21
<211> LENGTH: 9
<212> TYPE: PRT
<213> ORGANISM: Human
<220> FEATURE:
<221> NAME/KEY: VARIANT
<222> LOCATION: 9
<223> OTHER INFORMATION: Xaa at position 9 is an amino acid with an
      aliphatic or amide side chain.
<220> FEATURE:
<221> NAME/KEY: VARIANT
<222> LOCATION: 2
<223> OTHER INFORMATION: Xaa at position 2 is an amino acid with an
      aliphatic or amide side chain
<220> FEATURE:
<221> NAME/KEY: VARIANT
<222> LOCATION: 3
<223> OTHER INFORMATION: Xaa at position 3 is  an amino acid with an
      aliphatic or amide side chain.
<220> FEATURE:
<221> NAME/KEY: VARIANT
<222> LOCATION: 5
<223> OTHER INFORMATION: Xaa at position 5 is an amino acid with a basic
      side chain (except HIS) or an acidic side chain.
<220> FEATURE:
<221> NAME/KEY: VARIANT
<222> LOCATION: 6
<223> OTHER INFORMATION: Xaa at position 6 is an amino acid with a basic
      side chain (except HIS) or an acidic side chain.
<220> FEATURE:
<221> NAME/KEY: VARIANT
<222> LOCATION: 7
<223> OTHER INFORMATION: Xaa at position 7 is an amino acid with a basic
      side chain (except HIS) or an acidic side chain.

<400> SEQUENCE: 21

His Xaa Xaa His Xaa Xaa Xaa His Xaa
 1               5

<210> SEQ ID NO 22
<211> LENGTH: 6
<212> TYPE: PRT
<213> ORGANISM: Human
<220> FEATURE:

<400> SEQUENCE: 22

His Arg His Arg His Arg
 1               5

<210> SEQ ID NO 23
<211> LENGTH: 9
<212> TYPE: PRT
<213> ORGANISM: Human
<220> FEATURE:
<221> NAME/KEY: VARIANT
<222> LOCATION: 2
<223> OTHER INFORMATION: Xaa = an amino acid having an acidic side
      chain.
<220> FEATURE:
<221> NAME/KEY: VARIANT
<222> LOCATION: 3
```

```
<223> OTHER INFORMATION: Xaa = an amino acid having an acidic side
      chain.
<220> FEATURE:
<221> NAME/KEY: VARIANT
<222> LOCATION: 5
<223> OTHER INFORMATION: Xaa = an amino acid having an acidic side
      chain.
<220> FEATURE:
<221> NAME/KEY: VARIANT
<222> LOCATION: 6
<223> OTHER INFORMATION: Xaa = an amino acid having an acidic side
      chain.
<220> FEATURE:
<221> NAME/KEY: VARIANT
<222> LOCATION: 8
<223> OTHER INFORMATION: Xaa = an amino acid having an acidic side
      chain.
<220> FEATURE:
<221> NAME/KEY: VARIANT
<222> LOCATION: 9
<223> OTHER INFORMATION: Xaa = an amino acid having an acidic side
      chain.

<400> SEQUENCE: 23

His Xaa Xaa His Xaa Xaa His Xaa Xaa
 1               5

<210> SEQ ID NO 24
<211> LENGTH: 21
<212> TYPE: PRT
<213> ORGANISM: Artificial Sequence
<220> FEATURE:
<223> OTHER INFORMATION: Translation of nucleotide coding sequence

<400> SEQUENCE: 24

Leu Pro Pro Leu Ser Glu Leu Ile Pro Leu Ala Ala Ala Glu Arg Pro
 1               5                  10                  15

Ser Ala Ala Ser Gln
            20

<210> SEQ ID NO 25
<211> LENGTH: 38
<212> TYPE: PRT
<213> ORGANISM: Artificial Sequence
<220> FEATURE:
<223> OTHER INFORMATION: Translation of nucleotide coding sequence

<400> SEQUENCE: 25

Ala Arg Lys Arg Lys Ser Ala Gln Tyr Ala Asn Arg Leu Ser Pro Arg
 1               5                  10                  15

Val Gly Arg Phe Ile Asn Ala Ala Gly Thr Thr Gly Phe Pro Thr Gly
            20                  25                  30

Lys Arg Ala Val Ser Ala
        35

<210> SEQ ID NO 26
<211> LENGTH: 10
<212> TYPE: PRT
<213> ORGANISM: Artificial Sequence
<220> FEATURE:
<223> OTHER INFORMATION: Translation of nucleotide coding sequence

<400> SEQUENCE: 26

Glu Phe Thr Gly Arg Arg Phe Thr Thr Ser
 1               5                  10

<210> SEQ ID NO 27
<211> LENGTH: 6
```

-continued

```
<212> TYPE: PRT
<213> ORGANISM: Artificial Sequence
<220> FEATURE:
<223> OTHER INFORMATION: an amino acid sequence embodiment of the
      affinity purification site

<400> SEQUENCE: 27

His Asn His Asn His Asn
 1               5

<210> SEQ ID NO 28
<211> LENGTH: 8
<212> TYPE: PRT
<213> ORGANISM: Artificial Sequence
<220> FEATURE:
<223> OTHER INFORMATION: an amino acid sequence embodiment of the
      affinity purification site

<400> SEQUENCE: 28

His Asn His Asn His Asn His Asn
 1               5

<210> SEQ ID NO 29
<211> LENGTH: 10
<212> TYPE: PRT
<213> ORGANISM: Artificial Sequence
<220> FEATURE:
<223> OTHER INFORMATION: an amino acid sequence embodiment of the
      affinity purification site

<400> SEQUENCE: 29

His Asn His Asn His Asn His Asn His Asn
 1               5                  10

<210> SEQ ID NO 30
<211> LENGTH: 14
<212> TYPE: PRT
<213> ORGANISM: Artificial Sequence
<220> FEATURE:
<223> OTHER INFORMATION: an amino acid sequence embodiment of the
      affinity purification site

<400> SEQUENCE: 30

His Asn His Asn His Asn His Asn His Asn His Asn His Asn
 1               5                  10

<210> SEQ ID NO 31
<211> LENGTH: 16
<212> TYPE: PRT
<213> ORGANISM: Artificial Sequence
<220> FEATURE:
<223> OTHER INFORMATION: an amino acid sequence embodiment of the
      affinity purification site

<400> SEQUENCE: 31

His Asn His Asn His Asn His Asn His Asn His Asn His Asn His Asn
 1               5                  10                  15

<210> SEQ ID NO 32
<211> LENGTH: 18
<212> TYPE: PRT
<213> ORGANISM: Artificial Sequence
<220> FEATURE:
<223> OTHER INFORMATION: an amino acid sequence embodiment of the
      affinity purification site

<400> SEQUENCE: 32

His Asn His Asn His Asn His Asn His Asn His Asn His Asn His Asn His Asn
```

```
                1               5              10              15
His Asn

<210> SEQ ID NO 33
<211> LENGTH: 20
<212> TYPE: PRT
<213> ORGANISM: Artificial Sequence
<220> FEATURE:
<223> OTHER INFORMATION: an amino acid sequence embodiment of the
      affinity purification site

<400> SEQUENCE: 33

His Asn His Asn His Asn His Asn His Asn His Asn His Asn His Asn
 1               5              10                      15

His Asn His Asn
            20
```

US 7,176,298 B2

POLYNUCLEOTIDES ENCODING METAL ION AFFINITY PEPTIDES AND RELATED PRODUCTS

CROSS-REFERENCE TO RELATED APPLICATIONS

This patent application is a continuation-in-part of U.S. patent application Ser. No. 09/404,017, filed Sep. 23, 1999, now abandoned, which claims priority under 35 U.S.C. §119 to U.S. Provisional Patent Application Ser. No. 60/101,867, filed Sep. 25, 1998, now abandoned; which applications are incorporated herein in their entirety and to which priority is claimed.

FIELD OF THE INVENTION

This invention relates generally to the field of protein chemistry. Specifically, the present invention relates to the field of protein purification methods based on metal ion affinity sites compositions.

BACKGROUND OF THE INVENTION

Immobilized Metal Ion Affinity Chromatography (IMAC) is one of the most frequently used techniques for purification of fusion proteins containing affinity sites for metal ions. IMAC is a separation principle that utilizes the differential affinity of proteins for immobilized metal ions to effect their separation. This differential affinity derives from the coordination bonds formed between metal ions and certain amino acid side chains exposed on the surface of the protein molecules. Since the interaction between the immobilized metal ions and the side chains of amino acids has a readily reversible character, it can be utilized for adsorption and then be disrupted using mild (i.e., non denaturing) conditions.

Adsorbents that are currently commercially available include iminodiacetic acid (IDA), nitriloacetic acid (NTA), caboxymethylated aspartic acid (CM-Asp), and tris-carboxymethyl ethylene diamine (TED). These ligands offer a maximum of tri- (IDA), tetra- (NTA, CM-Asp), and penta-dentate (TED) complexes with the respective metal ion. In most commercially available adsorbents, metal chelating ligands are provided at an average density of about 12 Å. Depending on the ligand, various metals can be chelated. Metal ions typically used in IMAC procedures have been classified into three categories—hard, intermediate, and soft—based on their preferential reactivity toward nucleophiles. The hard metal ions $Fe^{3+}$, $Ca^{2+}$, and $Al^{3+}$ show a preference for oxygen; the soft metal ions $Cu^+$, $Hg^{2+}$, $Ag^+$, and the like show a preference for sulfur; and intermediate metal ions such as $Cu^{2+}$, $Ni^{2+}$, $Zn^{2+}$, and $Co^{2+}$ coordinate nitrogen, oxygen, and sulfur. The number of cysteine residues on the surfaces of proteins is limited; therefore, histidine residues are the major targets for intermediate metal ions.

The observation that histidine residues bind to certain immobilized ions led to the development of histidine-containing "tags" for proteins to aid in purification of such proteins. In particular, peptide tags containing multiple histidines have been developed. For example hexa-histidine tags are commonly used with IMAC adsorbents for purification of recombinant proteins.

Despite the advances made in protein purification using IMAC, there is an ongoing need in the art for improved metal ion affinity tags for use in purifying proteins. The present invention addresses this need.

Literature

The following publications are of interest: Itakura, et al., *Science* 198:1056–63 (1977); Germino, et al., *Proc. Natl. Acad. Sci. USA* 80:6848–52 (1983); Nilsson et al., *Nucleic Acids Res.* 13:1151–62 (1985); Smith et al., *Gene* 32:321–27 (1984); Dobeli, et al., U.S. Pat. No. 5,284,933; Dobeli, et al., U.S. Pat. No. 5,310,663; U.S. Pat. No. 4,569,794; and U.S. Pat. No. 5,594,115.

SUMMARY OF THE INVENTION

Metal Ion Affinity peptides, as well as methods for using the same in protein purification methods, are provided. Also provided are fusion proteins containing the peptides and vectors encoding the same. Finally, kits for use in practicing the subject methods are provided. The subject invention finds use in a variety of protein purification applications.

BRIEF DESCRIPTIONS OF THE DRAWINGS

FIG. 1 is a schematic presentation of a vector containing the cDNA of recombinant enterokinase fused to an affinity purification peptide.

FIG. 2 is the DNA sequence of the vector presented in FIG. 1 and certain amino acid sequences encoded therein. Nucleotides 1 to 3426 is SEQ ID NO:13. The peptide encoded by nucleotides 2218 to 3024 is SEQ ID NO:14, the peptide encoded by nucleotides 1921–1983 is SEQ ID NO:24, the peptide encoded by nucleotides 1987–2100 is SEQ ID NO:25, and the peptide encoded by nucleotides 3028–3058 is SEQ ID NO:26. The start of translation is denoted by lower case type in the amino acid sequence, the affinity purification peptide is denoted with lower case bolded type in the amino acid sequence, and the enterokinase cDNA is denoted with lowercase bold type in both the DNA and amino acid sequences.

FIG. 3 shows various DNA and amino acid sequence embodiments of the affinity purification peptides of the present invention, specifically: (1) a peptide having an amino acid sequence of SEQ ID NO:01 and encoded by a nucleic acid having a sequence of SEQ ID NO:16; (2) a peptide having an amino acid sequence of SEQ ID NO:15 and encoded by a nucleic acid having a sequence of SEQ ID NO:17; (3) a peptide having an amino acid sequence of SEQ ID NO:02 and encoded by a nucleic acid having a sequence of SEQ ID NO:18; (4) a peptide having an amino acid sequence of SEQ ID NO:03 and encoded by a nucleic acid having a sequence of SEQ ID NO:19; and (5) a peptide having an amino acid sequence of SEQ ID NO:04 and encoded by a nucleic acid having a sequence of SEQ ID NO:20.

Figure 4:
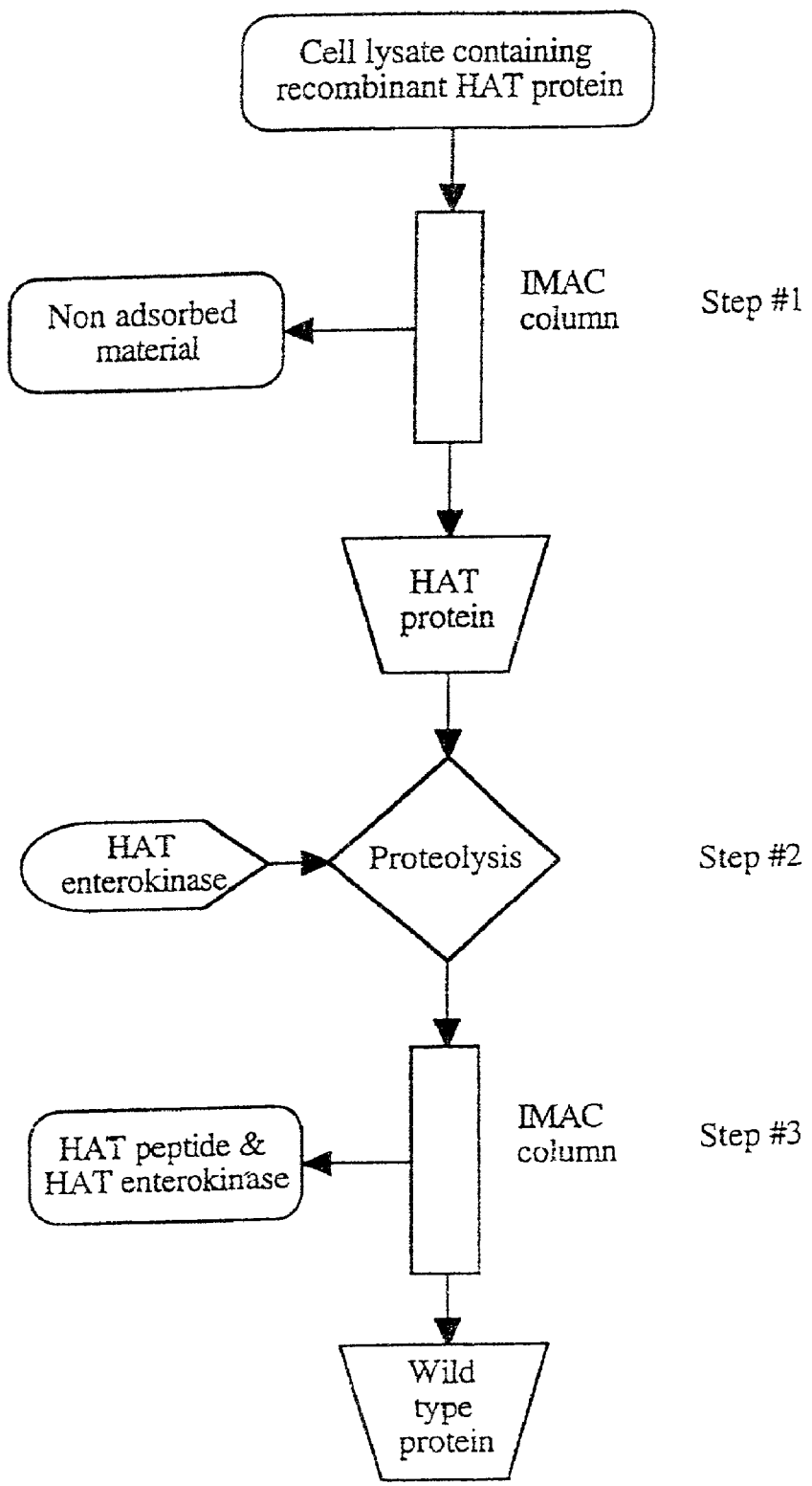

FIG. 4 illustrates the process for using the recombinant enterokinase-containing affinity purification peptide of the present invention (denoted as "HAT" for histidine affinity tag) for the production of wildtype proteins from recombinant (HAT) fusion proteins containing the affinity purification peptide.

Figure 5:
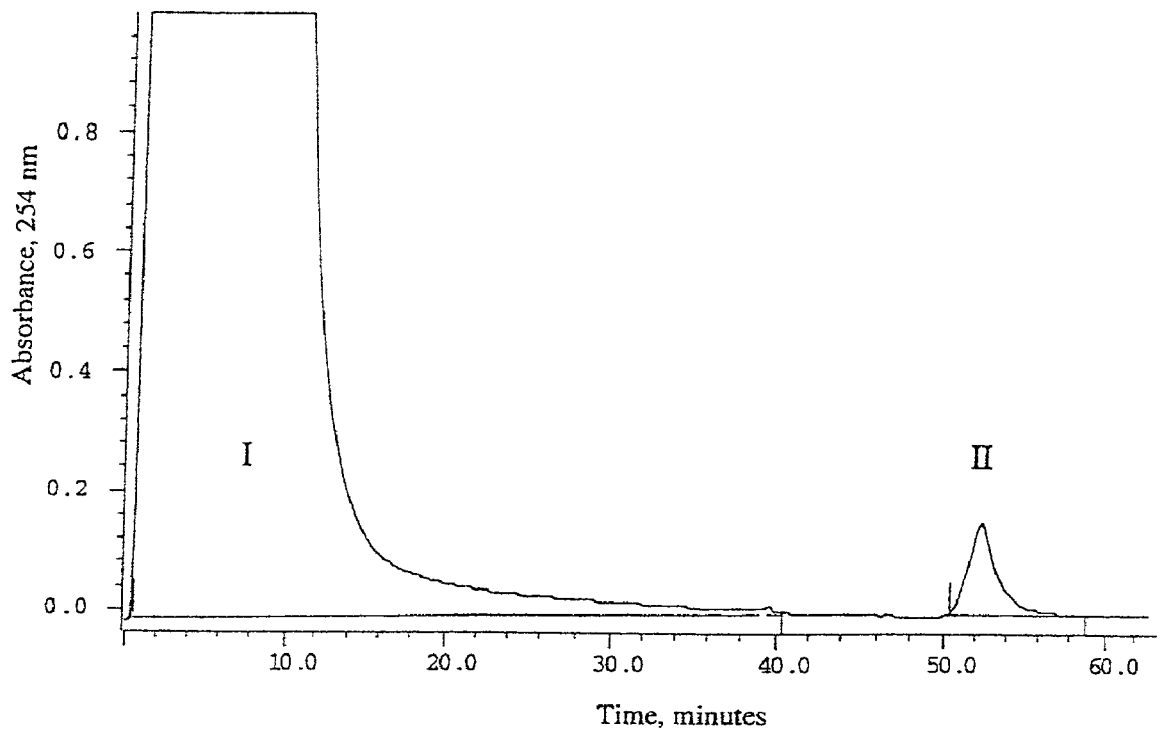

FIG. 5 shows the results of the purification of HAT-DHFR using the Insert 2 embodiment shown in FIG. 3. Peak I is non-adsorbed material. Peak 11 is the HAT-DHFR.

Figure 6:
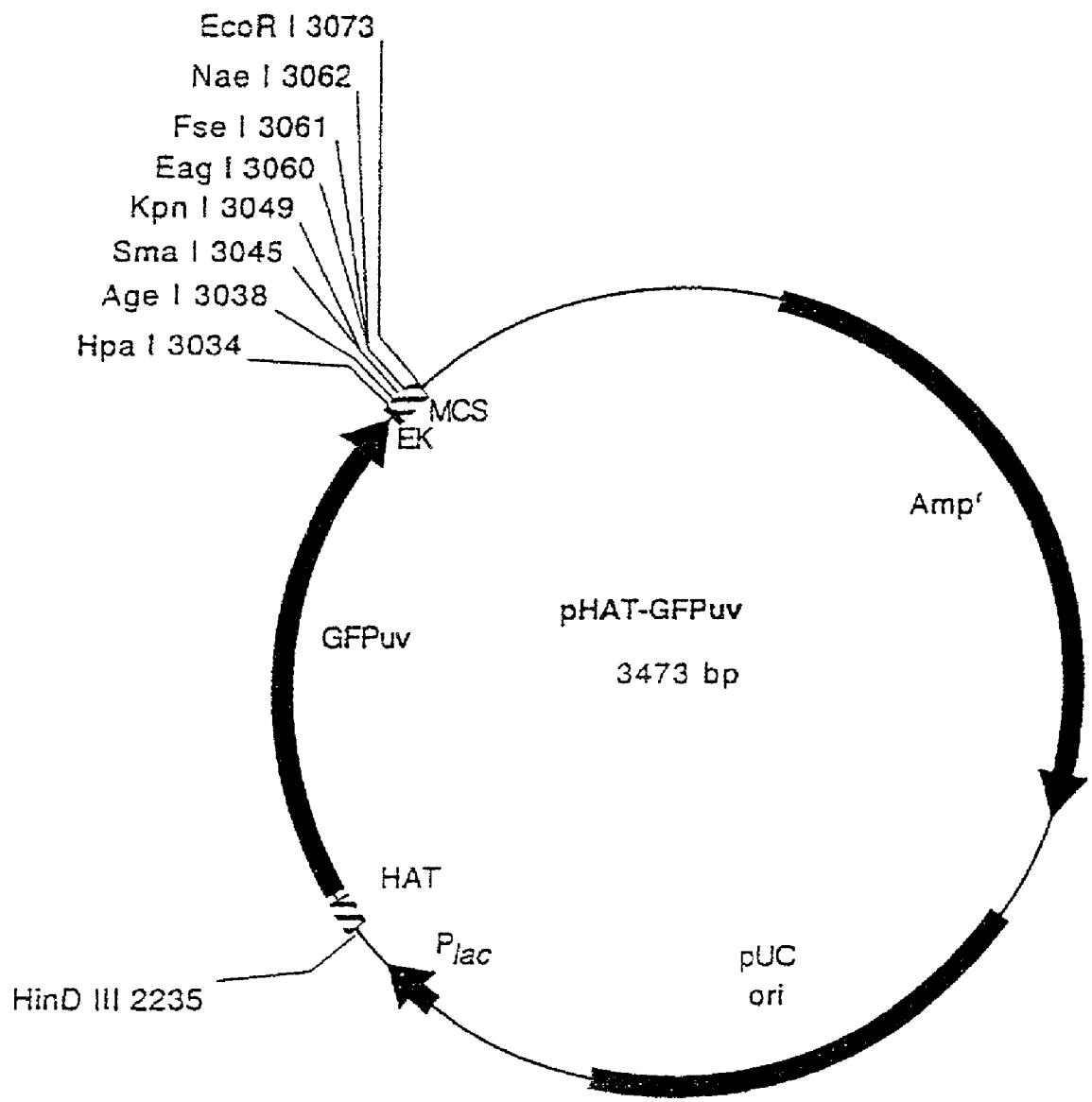

FIG. 6 is a map of the pHAT-GFPuv vector describe in Example 3.

DEFINITIONS

The terms "affinity peptide," "high affinity peptide," and "metal ion affinity peptide" are used interchangeably herein to refer to a histidine-rich peptide that binds to a metal ion.

The terms "protein of interest" and "fusion partner polypeptide," used interchangeably herein, refer to any protein to which the affinity peptide is fused for the purpose of purification or immobilization.

As used herein, the term "fusion protein" refers to the protein hybrid comprising a metal ion affinity peptide and a fusion partner polypeptide.

As used herein, the terms "secretion sequence" or "secretion signal sequence" refer to an amino acid signal sequence which leads to the transport of a protein containing the signal sequence outside the cell membrane. In the present case, a fusion protein of the present invention may contain such a secretion sequence to enhance and simplify purification.

As used herein, the term "proteolytic cleavage site" refers to any amino acid sequence recognized by any proteolytic enzyme. In the present case, a fusion protein of the present invention may contain such a proteolytic cleavage site between the protein of interest and the affinity peptide and/or other amino acid sequences so that the protein of interest may be separated easily from these heterologous amino acid sequences.

As used herein, the term "enterokinase" refers to a protease which cleaves peptide chains specifically at the primary amino acid sequence: Asp Asp Asp Asp Lys (SEQ ID NO: 6).

As used herein, the terms "recombinant proteolytic enzyme", "recombinant protease", "engineered proteolytic enzyme" or "engineered protease" refer to proteolytic enzymes or proteases that contain a histidine-rich affinity peptide.

As used herein, the term "metal ion" refers to any metal ion for which the affinity peptide has affinity and that can be used for purification or immobilization of a fusion protein. Such metal ions include, but are not limited to, $Ni^{+2}$, $Co^{+2}$, $Fe^{+3}$, $Al^{+3}$, $Zn^{+2}$ and $Cu^{+2}$. As used herein, the term "hard metal ion" refers to a metal ion that shows a binding preference for oxygen. Hard metal ions include $Fe^{3+}$, $Ca^{2+}$, and $Al^{3+}$. As used herein, the term "soft metal ion" refers to a metal ion that shows a binding preference of sulfur. Soft metal ions include $Cu^+$, $Hg^{2+}$, and $Ag^+$. As used herein, the term "intermediate metal ion" refers to a metal ion that coordinates nitrogen, oxygen, and sulfur. Intermediate metal ions include $Cu^{2+}$, $Ni^{2+}$, $Zn^{2+}$, and $Co^{2+}$.

As used herein, the terms "adsorbent" or "solid support" refer to a chromatography or immobilization medium used to immobilize a metal ion.

As used herein, the term "regeneration," in the context of the fusion protein, refers to the process of separating or eliminating the affinity peptide and other heterologous amino acid sequences from the fusion protein to render the protein of interest after purification in its wild-type form.

In accordance with the present invention there may be employed conventional molecular biology, microbiology, and recombinant DNA techniques within the skill of the art. Such techniques are explained fully in the literature. See, e.g., Maniatis, Fritsch & Sambrook, "Molecular Cloning: A Laboratory Manual (1982); "DNA Cloning: A Practical Approach," Volumes I and II (D. N. Glove ed. 1985); "Oligonucleotide Synthesis" (M. J. Gait ed. 1984); "Nucleic Acid Hybridization" (B. D. Hames & S. J. Higgins eds. (1985)); "Transcription and Translation" (B. D. Hames & S. J. Higgins eds. (1984)); "Animal Cell Culture" (R. I. Freshney, ed. (1986)); "Immobilized Cells And Enzymes" (IRL Press, (1986)); B. Perbal, "A Practical Guide to Molecular Cloning" (1984).

The term "vector" refers to a replicon, such as a plasmid, a phage, a viral vector, a minichromosome, an artificial chromosome, or a cosmid, to which another DNA segment may be attached so as to bring about the replication of the attached segment.

The terms "DNA molecule," "polynucleotide," and "nucleic acid molecule" are used interchangeably herein and refer to the polymeric form of deoxyribonucleotides (adenine, guanine, thymine, or cytosine) in either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the MRNA). The terms refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

A nucleic acid molecule may also comprise modified nucleic acid molecules, such as methylated nucleic acid molecules and nucleic acid molecule analogs. Analogs of purines and pyrimidines are known in the art. Nucleic acids may be naturally occurring, e.g. DNA or RNA, or may be synthetic analogs, as known in the art. Such analogs may be preferred for use as probes because of superior stability under assay conditions. Modifications in the native structure, including alterations in the backbone, sugars or heterocyclic bases, have been shown to increase intracellular stability and binding affinity. Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage.

Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity.

Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

A DNA "coding sequence" is a double-stranded DNA sequence which is transcribed and translated into a polypeptide in vivo (e.g., in a living cell) or in vitro (e.g., in a cell-free system) when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence. A polyadenylation sequence may also be located 3' to the coding sequence.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. Polypeptides may be polymers of: (a) naturally occurring amino acid residues; (b) non-naturally occurring amino acid residues, e.g. N-substituted glycines, amino acid substitutes, etc.; or (c) both naturally occurring and non-naturally occurring amino acid residues/substitutes. This term does not refer to or exclude post-translational modifications of the polypeptide, for example, glycosylations, acetylations, phosphorylations and the like. The term includes fusion proteins, including, but not limited to, fusion proteins with a heterologous amino acid sequence, fusions with heterologous and homologous leader sequences, with or without N-terminal methionine residues; immunologically tagged proteins; and the like.

As used herein the term "isolated polypeptide" is meant to describe a polypeptide that is in an environment different from that in which the polypeptide naturally occurs. As used herein, the term "substantially purified polypeptide" refers to a polypeptide that is removed from its natural environment and is at least 60% free, at least 75% free, or at least 90% free from other components with which it is naturally associated. The term "substantially purified polypeptide" also refers to a polypeptide that is at least about 60% free, at least about 70% free, at least about 75% free, at least about 80% free, at least about 85% free, at least about 90% free, at least about 95% free, at least about 98% free, or at least about 99% free, of macromolecules other than the polypeptide found in a sample comprising the polypeptide before the polypeptide is purified.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defiling the present invention, the promoter sequence is bounded at it 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "selection gene" refers to a gene that enables the discrimination of cells displaying a required phenotype upon implementation of certain conditions. For example, the growth of bacteria in medium containing antibiotics to select for the bacterial cells containing antibiotic resistance genes.

The term "oligonucleotide" or "probe" as used herein, refers to a molecule comprised of ribonucleotides or deoxyribonucleotides. The exact size of the oligonucleotide or probe will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, the source of primer and the method used.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A cell line" is a clone of a primary cell that is capable of stable growth in vitro for many generations.

The term "host cell" includes an individual cell or cell culture which can be or has been a recipient of any recombinant vector(s) or isolated polynucleotide of the invention. Host cells include progeny of a single host cell, and the progeny may not necessarily be completely identical (in morphology or in total DNA complement) to the original parent cell due to natural, accidental, or deliberate mutation and/or change. A host cell includes cells tranfected or infected in vivo or in vitro with a recombinant vector or a polynucleotide of the invention. A host cell which comprises a recombinant vector of the invention is a "recombinant host cell." Host cells include eukaryotic and prokaryotic cells.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art.

A "heterologous" region of the DNA construct is an identifiable segment of DNA within a larger DNA molecule that is not found in association with the larger molecule in nature. Thus, when the heterologous region is a mammalian gene, the gene will usually be flanked by DNA that does not flank the mammalian genomic DNA in the genome of the source organism. In another example, a heterologous region is a coding sequence where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

The amino acids described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxyl group present at the carboxyl terminus of a polypeptide. Abbreviations for amino acid residues are (in the following order: one-letter symbol, three-letter symbol, amino acid): Y, Tyr, tyrosine; G, Gly, glycine; F, Phe, phenylalanine; M, Met, methionine; A, Ala, alanine; S, Ser, serine; I, Ile, isoleucine; L, Leu, leucine; T, Thr, threonine; V, Val, valine; P, Pro, proline; K, Lys, lysine; H, His, histidine; Q, Gln, glutamine; E, Glu, glutamic acid; W, Trp, tryptophan; R, Arg, arginine; D, Asp, aspartic acid; N, Asn, asparagine; C, Cys, cysteine. It should be noted that all amino acid residue sequences are represented herein by formulae whose left and right orientation is in the conventional direction of amino terminus to carboxyl terminus. Furthermore, it should be noted that a dash at the beginning or end of an amino acid residue sequence indicates a peptide bond or non-standard peptide linkage to a further sequence of one or more amino acid residues.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "an affinity peptide" includes a plurality of such peptides and reference to "the purification method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The invention provides metal ion affinity peptides, fusion proteins containing the metal ion affinity peptides, as well as methods for using the subject affinity peptides in protein purification methods. The subject invention finds use in a variety of protein purification applications.

Fusion proteins comprising a subject metal ion affinity peptide are purified using immobilized metal ion affinity chromatography (IMAC). In many embodiments, a metal ion affinity peptide of the invention has affinity to both hard and intermediate metal ions. Thus, two IMAC resins, each having immobilized thereon a different metal ion, e.g., a hard and an intermediate metal ion, can be used with a single metal ion affinity peptide. Use of two different metal ions for purification of a protein tagged with a single metal ion affinity peptide is advantageous, as a high degree of purification can be attained with a single chromatographic step.

Details of the subject metal ion affinity peptides, fusion proteins containing the same, and purification methods are provided in the following sections.

Metal Ion Affinity Peptides

The present invention provides metal ion affinity peptides. The presence of the metal ion affinity peptide in a fusion protein allows purification of the fusion protein on a metal chelating resin. Thus, the subject metal ion affinity peptides are useful, when fused to a fusion partner polypeptide, in protein purification methods of the invention.

Metal ion affinity peptides of the invention bind to intermediate metal ions with an affinity of from about $10^{-3}$ $M^{-1}$ to about $10^{-9}$ $M^{-1}$; and to hard metal ions with an affinity of from about $10^{-3}$ $M^{-1}$ to about $10^{-9}$ $M^{-1}$.

Metal ion affinity peptides of the invention contain from about 30% to about 50%, from about 33% to about 45%, from about 35% to about 43%, or from about 37% to about 40%, histidine residues. For example, a metal ion affinity peptide 18 amino acids in length contains 6, 7, or 8 histidine residues.

Metal ion affinity peptides of the invention are generally from about 6 to about 30, from about 7 to about 25, from about 8 to about 20, from about 9 to about 18, from about 10 to about 16, or from about 12 to about 14 amino acids in length.

In some embodiments, a metal ion affinity peptide comprises a peptide of the formula: $(His-(X_1)_n)_m$, wherein $m \geq 3$, wherein $X_1$ is any amino acid other than His, wherein $n=1-3$, provided that, in at least one $His-(X_1)_n$ unit, $n>1$.

In some embodiments, a metal ion affinity peptide comprises a peptide of the formula:

$(His-X_1-X_2)_{n1}-(His-X_3-X_4-X_5)_{n2}-(His-X_6)_{n3}$, (SEQ ID NO:21)

wherein each of $X_1$ and $X_2$ is independently an amino acid with an aliphatic or an amide side chain, each of $X_3$, $X_4$, $X_5$ is independently an amino acid with a basic side chain (except His) or an acidic side chain, each $X_6$ is an amino acid with an aliphatic or an amide side chain, n1 and n2 are each independently 1–3, and n3 is 1–5.

In some embodiments, each of $X_1$ and $X_2$ is independently selected from the group consisting of Leu, Ile, Val, Ala, Gly, Asn, and Gln. In other embodiments, each of $X_1$ and $X_2$ is independently selected from the group consisting of Leu, Val, Asn, and Ile. In some embodiments, each of $X_3$, $X_4$, $X_5$ is independently selected from the group consisting of Lys, Arg, Asp, and Glu. In some embodiments, each of $X_3$, $X_4$, $X_5$ is independently selected from the group consisting of Lys and Glu. In some embodiments, each $X_6$ is independently selected from the group consisting of Leu, Ile, Val, Ala, Gly, Asn, and Gln. In other embodiments, each $X_6$ is independently selected from the group consisting of Ala and Asn. In one particular embodiment, the affinity peptide has the amino acid sequence NH$_2$-His-Leu-Ile-His-Asn-Val-His-Lys-Glu-Glu-His-Ala-His-Ala-His-Asn-COOH (SEQ ID NO: 1).

The invention further provides a metal ion affinity peptide, wherein the affinity peptide has the formula (His-Asn)$_n$, (SEQ ID NO:22) wherein n=3 to 10. In certain embodiments, n=from about 4 to about 10, and preferably from about 5 to about 10. In one particular embodiment, n=6.

The invention further provides a metal ion affinity peptide, wherein the affinity peptide has the formula (His-X$_1$-X$_2$)$_n$, (SEQ ID NO:23) wherein each of X$_1$ and X$_2$ is an amino acid having an acidic side chain, and n=3 to 10. In one embodiment, the affinity peptide comprises the sequence (His-Asp-Asp)$_6$(SEQ ID NO:02). In another embodiment, the affinity peptide comprises the sequence (His-Glu-Glu)$_6$ (SEQ ID NO:03). In a further embodiment, the affinity peptide comprises the sequence (His-Asp-Glu)$_6$(SEQ ID NO:04). In a further embodiment, the affinity peptide comprises the sequence (His-Glu-Asp)$_6$(SEQ ID NO:05).

Fusion Proteins

The present invention provides a fusion protein comprising a polypeptide (a "fusion partner polypeptide") fused at its amino- or carboxyl-terminus to a metal ion affinity peptide as described above. The presence of the metal ion affinity peptide allows purification of the fusion protein on a metal chelating resin.

In some embodiments, a subject fusion protein has the formula: NH$_2$-ψ-ω-COOH, wherein ψ is a fusion partner polypeptide, and ω is a metal ion affinity peptide of the invention. In some of these embodiments, a subject fusion protein has the formula: NH$_2$-ψ-Z-ω-COOH, wherein Z is an intervening moiety, including but not limited to, a linker; a proteolytic cleavage site; an amino acid sequence that improves the solubility of the fusion protein; or a combination of the foregoing in any order.

In other embodiments, a subject fusion protein has the formula NH$_2$-ω-ψ-COOH. In some of these embodiments, a subject fusion protein has the formula: NH$_2$-ω-Z-ψ-COOH, wherein Z is an intervening moiety, including but not limited to, a linker; a proteolytic cleavage site; an immunological tag, or a combination of the foregoing in any order.

A linker can be any amino acid sequence that is not native to the fusion partner polypeptide, and is generally about two to about 30 amino acids in length. One non-limiting example of linker molecules is (Gly)$_n$, where n=2 to 30.

Proteolytic cleavage sites are known to those skilled in the art; a wide variety are known and have been described amply in the literature, including, e.g., *Handbook of Proteolytic Enzymes* (1998) A J Barrett, N D Rawlings, and J F Woessner, eds., Academic Press. Proteolytic cleavage sites include, but are not limited to, an enterokinase cleavage site: (Asp)$_4$Lys (SEQ ID NO: 6); a factor Xa cleavage site: Ile-Glu-Gly-Arg (SEQ ID NO: 7); a thrombin cleavage site, e.g., Leu-Val-Pro-Arg-Gly-Ser(SEQ ID NO: 8); a renin cleavage site, e.g., His-Pro-Phe-His-Leu-Val-Ile-His (SEQ ID NO: 9); a collagenase cleavage site, e.g., X-Gly-Pro (where X is any amino acid); a trypsin cleavage site, e.g., Arg-Lys; a viral protease cleavage site, such as a viral 2A or 3C protease cleavage site, including, but not limited to, a protease 2A cleavage site from a picornavirus (see, e.g., Sommergruber et al. (1994) *Virol.* 198:741–745), a Hepatitis A virus 3C cleavage site (see, e.g., Schultheiss et al. (1995) *J. Virol.* 69:1727–1733), human rhinovirus 2A protease cleavage site (see, e.g., Wang et al. (1997) *Biochem. Biophys Res. Comm.* 235:562–566), and a picornavirus 3 protease cleavage site (see, e.g., Walker et al. (1994) *Biotechnol.* 12:601–605.

A subject fusion protein may comprise, in addition to a fusion partner polypeptide and a metal ion affinity peptide, an immunological tag. An immunological tag, if present, is present at the amino terminus, the carboxyl terminus, or disposed between the fusion partner polypeptide and the metal ion affinity peptide. Immunological tags are known in the art, and are typically a sequence of between about 6 and about 50 amino acids that comprise an epitope that is recognized by an antibody specific for the epitope. Non-limiting examples of such tags are hemagglutinin (HA; e.g., CYPYDVPDYA, SEQ ID NO: 10), FLAG (e.g., DYKD-DDDK, SEQ ID NO: 11), c-myc (e.g., CEQKLISEEDL, SEQ ID NO: 12), and the like.

A subject fusion protein may comprise an amino acid sequence that provides for secretion of the fusion protein from the cell. Those skilled in the art are aware of such secretion signal sequences. Secretion signals that are suitable for use in bacteria include, but are not limited to, the secretion signal of Braun's lipoprotein of *E. coli, S. marcescens, E. amylosora, M. morganii*, and *P. mirabilis*, the TraT protein of *E. coli* and *Salmonella*; the penicillinase (PenP) protein of *B. licheniformis* and *B. cereus* and *S. aureus*; pullulanase proteins of *Klebsiella pneumoniae* and *Klebsiella aerogenese*; *E. coli* lipoproteins 1pp-28, Pa1, Rp1A, Rp1B, OsmB, NlpB, and Or117; chitobiase protein of *V. harseyi*; the β-1,4-endoglucanase protein of *Pseudomonas solanacearum*, the Pa1 and Pcp proteins of *H. influenzae*; the OprI protein of *P. aeruginosa*; the Ma1X and AmiA proteins of *S. pneumoniae*; the 34 kda antigen and TpmA protein of *Treponema pallidum*; the P37 protein of *Mycoplasma hyorhinis*; the neutral protease of *Bacillus amyloliquefaciens*; and the 17 kda antigen of *Rickettsia rickettsii*. Secretion signal sequences suitable for use in yeast are known in the art, and can be used. See, e.g., U.S. Pat. No. 5,712,113.

Fusion partner polypeptides are of any length, e.g, from about 10 to about 5000, from about 20 to about 4500, from about 25 to about 4000, from about 50 to about 3500, from about 75 to about 3000, from about 100 to about 2500, from about 150 to about 2000, from about 200 to about 1500, from about 250 to about 1250, from about 300 to about 1000, from about 350 to about 950, from about 400 to about 900, from about 450 to about 850, from about 500 to about 800, from about 550 to about 750, or from about 600 to about 700, amino acids.

A fusion partner polypeptide can be a natural or non-natural (e.g., having an amino acid sequence not found in nature) polypeptide; a polypeptide from an animal, plant, eubacterium, archaebacterium, fungus, protozoa, or virus. A fusion partner polypeptide can be a fragment of any known naturally-occurring or non-naturally occurring polypeptide. Fragments or interest include, but are not limited to, functional domains, e.g., a catalytic domain of an enzyme, a DNA-binding domain of a transcription factor, a ligand-binding domain of a receptor, and the like; structural domains; fragments that inhibit a protein function; and the like.

The fusion partner polypeptide does not bind to the immobilized metal ion; instead, binding is mediated primarily by the metal ion affinity peptide. A fusion partner polypeptides can be any known protein, including, but not limited to, peptide hormones, enzymes, neurotransmitters, cytokines, chemokines, structural proteins, receptors, transcription factors, serum proteins, regulatory proteins, antibodies, antibiotic and bacteriostatic peptides, insecticidal, herbicidal and fungicidal peptides, and the like.

A fusion partner polypeptide can also be a protein of unknown identity or function, e.g., a protein encoded by a putative coding region identified in a sequencing project.

Suitable fusion partner polypeptides, include, but are not limited to, erythropoietin, oxytocin, vasopressin, adrenocorticotropic hormone, relaxin, epidermal growth factor, platelet-derived growth factor (PDGF), prolactin, luteinizing hormone releasing hormone (LHRH), LHRH agonists, LHRH antagonists, growth hormone (human, porcine, bovine, etc.), growth hormone releasing factor, insulin, somatostatin, glucagon, interleukin-2 (IL-2), interferon-α, β, or γ, gastrin, tetragastrin, pentagastrin, urogastrone, secretin, calcitonin, enkephalins, endorphins, angiotensins, tumor necrosis factor, nerve growth factor (NGF), granulocyte-colony stimulating factor, granulocyte macrophage-colony stimulating factor (GM-CSF), macrophage-colony stimulating factor (M-CSF), heparinase, bone morphogenic protein (BMP), atrial natriuretic peptide, glucagon-like peptide (GLP-1), interleukin-11 (IL-11), renin, bradykinin, bacitracins, polymyxins, colistins, tyrocidine, bacteriocins, gramicidins, cyclosporins, cecropins, attacins, apidaecins; polymerases, ligases, phosphorylases, kinases, phosphatases, glycosylases, sulfotransferases, lipases, dehydrogenases, reverse transcriptases; calcium channels, T-cell antigen receptor, epidermal growth factor receptor, chemokine receptors, potassium channels, serotonin receptors; tumor-associated antigens; histones, actin, myosin, tubulin, capsid proteins, group-specific antigens, viral envelope proteins; clotting factors (e.g., Factor VIII, Factor IX, etc.); etc.

Polynucleotide Compositions

The invention further provides polynucleotides that comprise a nucleotide sequence that encodes a metal ion affinity peptide, as described above. The invention further provides compositions comprising such polynucleotides. These polynucleotides can be used in a recombinant vector, as described in more detail below.

Also provided are polynucleotides that comprise a sequence that encodes a metal ion affinity peptide that binds to an intermediate metal ion with an affinity that is at least about 50%, at least about 60%, at least about 70%, at least about 75%, at least about 80%, at least about 85%, at least about 90%, at least about 95%, or more, of the affinity of a subject metal ion affinity peptide.

The invention further provides polynucleotides that comprise a nucleotide sequence that encodes a fusion protein as described above. The invention further provides compositions comprising the polynucleotides of the invention. These polynucleotides can be used, when in a recombinant expression vector, to produce the encoded fusion protein.

The subject polynucleotides can be prepared in a number of different ways. For example, the nucleic acid may be synthesized using solid phase synthesis techniques, as are known in the art. Oligonucleotide synthesis is also described in Edge, et al., (1981) *Nature* 292:756; Duckworth et al., (1981) *Nucleic Acids Res* 9:1691 and Beaucage, et al., (1981) *Tet. Letts* 22:1859. Following preparation of the nucleic acid, the nucleic acid is then ligated to other members of the expression system to produce an expression cassette or system comprising a nucleic acid encoding the subject product in operational combination with transcriptional initiation and termination regions, which provide for expression of the nucleic acid into the subject polypeptide products under suitable conditions.

Also provided are polynucleotides comprising a nucleotide sequence that hybridizes under stringent hybridization conditions with a nucleic acid molecule that encodes a subject metal ion affinity peptide or a subject fusion protein. Hybridization reactions can be performed under conditions of different "stringency". Conditions that increase stringency of a hybridization reaction of widely known and published in the art. See, for example, Sambrook et al. (1989). Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or deionized water.

An example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Stringent hybridization conditions are hybridization conditions that are at least as stringent as the above representative conditions. Other stringent hybridization conditions are known in the art and may also be employed to identify nucleic acids of this particular embodiment of the invention.

Also provided are polynucleotides comprising a nucleotide sequence that has substantial sequence similarity to a nucleotide sequence encoding a subject metal ion affinity peptide or a subject fusion protein, e.g. at least 60% sequence identity, usually at least 75%, more usually at least 80% between nucleotide sequences. In many embodiments of interest, homology will be at least 75, usually at least 80 and more usually at least 85%, where in certain embodiments of interest homology will be as high as 90%. Sequence similarity is calculated based on a reference sequence, which may be a subset of a larger sequence, such as a conserved motif, coding region, flanking region, etc. A reference sequence will usually be at least about 18 nucleotides (nt) long, more usually at least about 30 nt long, and may extend to the complete sequence that is being compared. Algorithms for sequence analysis are known in the art, such as BLAST, described in Altschul et al. (1990), *J. Mol. Biol.* 215:403–10 (using default settings).

Recombinant Vectors and Recombinant Host Cells

The present invention further provides recombinant vectors ("constructs") comprising a subject polynucleotide, as well as recombinant host cells comprising a recombinant vector of the invention. Recombinant vectors are useful for propagation of the subject polynucleotides (cloning vectors). They are also useful for effecting expression of a subject polynucleotide in a cell (expression vectors). Some vectors accomplish both cloning and expression functions. The choice of appropriate vector is well within the skill of the art. Many such vectors are available commercially.

In some embodiments, a recombinant vector comprises a nucleotide sequence encoding a metal ion affinity peptide, and a restriction endonuclease recognition sequence for inserting a heterologous nucleic acid molecule comprising a sequence that encodes a fusion partner protein, such that when a heterologous nucleic acid molecule is inserted into the vector, the recombinant vector encodes a fusion protein as described herein. In some embodiments, more than one restriction endonuclease site is provided in a tandem and/or partially overlapping arrangement, such that a "multiple cloning site" is provided. In some embodiments, a recombinant vector further comprises control sequences, such as a promoter, for controlling transcription of a coding region for a fusion protein. Thus, in some embodiments, the recombinant vector comprises, in order from 5' to 3', a transcription control sequence, a restriction endonuclease recognition site, and a nucleotide sequence encoding a metal ion affinity peptide.

In other embodiments, the recombinant vector comprises, in order from 5' to 3', a transcription control sequence, a nucleotide sequence encoding a metal ion affinity peptide, and a restriction endonuclease recognition site. The restriction endonuclease recognition site for inserting a heterologous nucleic acid molecule is positioned relative to the sequences encoding the metal ion affinity peptide to provide for in-frame fusion of the affinity peptide with the fusion partner polypeptide, and is typically within less than about 50 bases from the sequences encoding the metal ion affinity peptide. The recombinant vector typically further comprises a nucleotide sequence encoding a selectable marker (e.g., antibiotic resistance), and an origin of replication.

A recombinant vector can further comprise a nucleotide sequence that encodes a proteolytic cleavage site, such that the fusion partner polypeptide can be cleaved away from the metal ion affinity peptide. Thus, in some embodiments, a recombinant vector comprises, in order from 5' to 3', a nucleotide sequence encoding a subject metal ion affinity peptide; a nucleotide sequence encoding a proteolytic cleavage site; and one or more restriction endonuclease recognition sites.

For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the subject gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. After introduction of the DNA, the cells containing the construct may be selected by means of a selectable marker, the cells expanded and then used for expression.

The polypeptides may be expressed in prokaryotes or eukaryotes in accordance with conventional ways, depending upon the purpose for expression. For large-scale production of the protein, a unicellular organism, such as *E. coli, B. subtilis, S. cerevisiae,* insect cells in combination with baculovirus vectors, or cells of a higher organism such as vertebrates, particularly mammals, e.g. COS 7 cells, may be used as the expression host cells. In some situations, it is desirable to express the gene in eukaryotic cells, where the protein will benefit from native folding and post-translational modifications. Small peptides can also be synthesized in the laboratory. Polypeptides that are subsets of the complete amino acid sequence may be used to identify and investigate parts of the protein important for function, or to raise antibodies directed against these regions.

A variety of host-vector systems may be utilized to propagate and/or express the subject polynucleotide. Such host-vector systems represent vehicles by which coding sequences of interest may be produced and subsequently purified, and also represent cells that may, when transformed or transfected with the appropriate nucleotide coding sequences, produce fusion polypeptides of the invention. These include, but are not limited to, microorganisms (e.g., *E. coli, B. subtilis*) transformed with recombinant bacteriophage vectors, plasmid DNA, or cosmid DNA vectors comprising the subject polynucleotides; yeast (e.g.,*Saccharomyces, Pichia*) transformed with recombinant yeast vectors comprising subject polynucleotides); insect cell systems (e.g., *Spodoptera frugiperda*) infected with recombinant virus expression vectors (e.g., baculovirus vectors, many of which are commercially available, including, for example, pBacPAK8, and BacPAK6) comprising subject polynucleotides; plant cell systems; or mammalian cell systems (e.g., COS, CHO, BHK, 293, 3T3) harboring recombinant vectors comprising mammalian promoters (e.g., metallothionein promoter) or promoters from viruses which replicate in mammalian cells (e.g., adenovirus late promoter; vaccinia virus promoter, and the like).

Examples of prokaryotic cloning vectors which find use in propagating polynucleotides of the invention are pBR322, M13 vectors, pUC18, pcDNA, and pUC19. Prokaryotic expression vectors which find use in expressing subject polypeptides in prokaryotic cells include pTrc99A, pK223-3, pEZZ18, pRIT2T, and pMC1871.

Eukaryotic expression vectors which find use in expressing subject polynucleotides and subject fusion polypeptides in eukaryotic cells include commercially available vectors such as pSVK3, pSVL, pMSG, pCH110, pMAMneo, pMAMneo-LUC, pPUR, and the like.

Generally, a bacterial host will be transformed to contain the expression system using a vector. A variety of vectors may be employed so long as they introduce the expression system into the host in a manner whereby the product encoded by the expression system can be expressed.

Generally, the expression cassette will be a plasmid that provides for expression of the encoded subject fusion polypeptide under appropriate conditions, i.e. in a host cell. The expression vector will typically comprise a replicon, which includes the origin of replication and its associated cis-acting control elements. Representative replicons that may be present on the expression vector include: pMB1, p15A, pSC101 and Co1E1. Expression vectors generally have convenient restriction sites located near the promoter sequence to provide for the insertion of nucleic acid sequences encoding heterologous proteins.

In addition, the expression vector will also typically comprise a marker which provides for detection of the clones that have been transformed with the vector. A variety of markers are known and may be present on the vector, where such markers include those that confer antibiotic resistance, e.g. resistance to ampicillin, tetracycline, chloramphenicol, kanamycin (neomycin), markers that provide for histochemical detection, etc. Specific vectors that may find use in the subject methods include: pBR322, pUC18, pUC19, pcDNA, and the like. Introduction of the nucleic acid encoding the subject peptidic product into the expression vector is accomplished by cutting the expression vector and inserting the polynucleotide encoding the desired product.

Following preparation of the expression vector comprising the nucleic acid, the expression vector will be introduced into an appropriate host cell for production of the subject fusion polypeptide, i.e. a host cell will be transformed with the expression vector. Transformation of host cells may be accomplished in any convenient manner, where two representative means of transformation are treatment with divalent cation transformation compositions and electrotransformation. In transformation through divalent cation treatment, the host cells are typically incubated with the one or more divalent cations, e.g. CaCl$_2$, which serves to make the host cell permeable to the vector DNA. See Cohen et al. (1972) *Proc. Nat'l Acad. Sci. USA* 69:2110. Other agents with which the host cells may also be incubated include DMSO, reducing agents, hexaminecobalt and the like, where such agents serve to improve the efficiency of transformation. In electrotransformation (also known as transformation by electroporation) host cells are subject to an electrical pulse in the presence of the vector in a manner sufficient for the vector to enter the host cells. See Dower et al. (1988) *Nucleic Acids Research* 16:6127.

A variety of host cells are suitable and may be used in the production of the subject fusion polypeptides. Specific expression systems of interest include bacterial, yeast, insect cell and mammalian cell derived expression systems. Representative systems from each of these categories is are provided below:

Bacteria. Expression systems in bacteria include those described in Chang et al., *Nature (*1978) 275:615; Goeddel et al., *Nature* (1979) 281:544; Goeddel et al., *Nucleic Acids Res.* (1980) 8:4057; EP 0 036,776; U.S. Pat. No. 4,551,433; DeBoer et al., *Proc. Natl. Acad. Sci.* (*USA*) (1983) 80:21–25; and Siebenlist et al., *Cell* (1980) 20:269.

Yeast. Expression systems in yeast include those described in Hinnen et al., *Proc. Natl. Acad. Sci.* (*USA*) (1978) 75:1929; Ito et al., *J. Bacteriol.* (1983) 153:163; Kurtz et al., *Mol. Cell. Biol.* (1986) 6:142; Kunze et al., *J. Basic Microbiol.* (1985) 25:141; Gleeson et al., *J. Gen. Microbiol.* (1986) 132:3459; Roggenkamp et al., *Mol. Gen. Genet.* (1986) 202:302; Das et al., *J. Bacteriol.* (1984) 158:1165; De Louvencourt et al., *J. Bacteriol.* (1983) 154: 737; Van den Berg et al., *Bio/Technology* (1990) 8:135; Kunze et al., *J. Basic Microbiol.* (1985) 25:141; Cregg et al., *Mol. Cell. Biol.* (1985) 5:3376; U.S. Pat. Nos. 4,837,148 and 4,929,555; Beach and Nurse, *Nature* (1981) 300:706; Davidow et al., *Curr. Genet.* (1985) 10:380; Gaillardin et al., *Curr. Genet.* (1985) 10:49; Ballance et al., *Biochem. Biophys. Res. Commun.* (1983) 112:284–289; Tilburn et al., *Gene* (1983) 26:205–221; Yelton et al., *Proc. Natl. Acad. Sci.* (*USA*) (1984) 81:1470–1474; Kelly and Hynes, *EMBO J.* (1985) 4:475479; EP 0 244,234; and WO 91/00357.

Insect Cells. Expression of heterologous genes in insects is accomplished as described in U.S. Pat. No. 4,745,051; Friesen et al., "The Regulation of Baculovirus Gene Expression", in: *The Molecular Biology Of Baculoviruses* (1986) (W. Doerfler, ed.); EP 0 127,839; EP 0 155,476; and Vlak et al., *J. Gen. Virol.* (1988) 69:765–776; Miller et al., *Ann. Rev. Microbiol.* (1988) 42:177; Carbonell et al., *Gene* (1988) 73:409; Maeda et al., *Nature* (1985) 315:592–594; Lebacq-Verheyden et al., *Mol. Cell. Biol.* (1988) 8:3129; Smith et al., *Proc. Natl. Acad. Sci.* (*USA*) (1985) 82:8844; Miyajima et al., *Gene* (1987) 58:273; and Martin et al., *DNA* (1988) 7:99. Numerous baculoviral strains and variants and corresponding permissive insect host cells from hosts are described in Luckow et al., *Bio/Technology* (1988) 6:47–55, Miller et al., *Generic Engineering* (1986) 8:277–279, and Maeda et al., *Nature* (1985) 315:592–594.

Mammalian Cells. Mammalian expression is accomplished as described in Dijkema et al., *EMBO J.* (1985) 4:761, Gorman et al., *Proc. Natl. Acad. Sci.* (*USA*) (1982) 79:6777, Boshart et al., *Cell* (1985) 41:521 and U.S. Pat. No. 4,399,216. Other features of mammalian expression are facilitated as described in Ham and Wallace, *Meth. Enz.* (1979) 58:44, Barnes and Sato, *Anal. Biochem.* (1980) 102:255, U.S. Pat. Nos. 4,767,704, 4,657,866, 4,927,762, 4,560,655, WO 90/103430, WO 87/00195, and U.S. Reissue Pat. No. RE30,986.

Plant cells. Plant cell culture is amply described in various publications, including, e.g., *Plant Cell Culture: A Practical Approach*, (1995) R. A. Dixon and R. A. Gonzales, eds., IRL Press; and U.S. Pat. No. 6,069,009.

Methods

The subject metal ion affinity peptides and fusion proteins thereof find use in a variety of methods, such as protein purification methods.

Once a subject fusion protein is synthesized, e.g., by a recombinant host cell of the invention, the fusion protein can be purified using a metal ion chelate resin. Purification methods provided by the present invention generally involve contacting a sample containing a subject fusion protein with an immobilized metal ion affinity resin under conditions which favor binding of the fusion protein to the immobilized metal, and eluting the fusion protein. One or more washing steps may optionally be included to remove undesired components of the sample applied to the resin. Two or more different resins may be used.

The subject methods provide for purification of a subject fusion protein from a sample which contains, in addition to a subject fusion protein, other components e.g., proteins other than a subject fusion protein, and other non-protein components such as non-protein macromolecules. The starting sample is any sample containing a subject fusion protein and one or more other components. Using a method of the invention, a subject fusion protein can be purified in one, two, or more chromatographic steps. In some embodiments, a subject fusion protein is purified in one chromatographic step. A single chromatographic step includes contacting a sample with an IMAC resin such that a fusion protein contained within the sample binds to the IMAC resin, and eluting the bound fusion protein.

Using a method as described herein, a subject fusion protein is purified to a desired degree, depending on the application. In some embodiments, a subject fusion protein purified using a subject method is at least about 60%, at least about 70%, at least about 80%, at least about 85%, at least about 90%, at least about 95%, at least about 98%, at least about 99%, or more, pure, e.g., free of macromolecules other than the polypeptide found in a sample comprising the polypeptide before the polypeptide is purified. Purity can be determined using any known method, including, but not limited to, SDS-PAGE separation following by staining (e.g., Coomassie blue, silver staining, etc.).

The recovery of the fusion protein (e.g., the yield) is at least about 30%, at least about 40%, at least about 50%, at least about 60%, at least about 70%, at least about 75%, at least about 80%, at least about 85%, at least about 90%, at least about 95%, at least about 98%, or more.

Sample Preparation

In some embodiments, the fusion protein is secreted into the culture medium in which cells are grown. In other embodiments, the fusion protein remains intracellular (e.g., in the cytoplasm, in a cell membrane, or in an organelle), in which case the cells are disrupted. A variety of protocols for disrupting cells to release an intracellular protein are known in the art, and can be used to extract a fusion protein from a cell. Such protocols are found in numerous publications, including, e.g., Current *Protocols in Molecular Biology*, (F. M. Ausubel, et al., Eds. 1987, and updates). Whether cell culture medium ("culture supernatant") or disrupted cells ("cell lysate") are used as the starting material, the starting material may be subjected to one or more treatments before being applied to a metal ion chelating resin. Such treatments include, but are not limited to, centrifugation, to remove cell debris, etc.; salt precipitation; application to a size exclusion chromatographic column; and application to an ion exchange chromatographic column.

Metal Ion Affinity Resins

Any of a variety of available metal ion chelating resins can be used. In general, a metal ion chelating resin includes a carrier matrix, optionally a spacer, and a moiety that comprises a metal ion, e.g., an organic ligand that immobilizes a metal ion. Carrier matrices include, but are not limited to, cross-linked dextrans, polystyrenes, nylon, agarose, and polyacrylamides. Metal chelating ligands include, but are not limited to, carboxymethyl aspartate (CM-Asp); iminodiacetic acid (IDA); tris(carboxymethyl)ethylene diamine (TED); nitrilo triacetic acid (NTA). Several of these are commercially available.

The metal ion chelating resin can be provided in the form of a chromatography column, e.g., wherein the resin is packed in a column. The resin can also comprise a matrix that is a solid support of any shape or configuration. Thus, the term "resin," as used herein, refers to a resin comprising a matrix in any form, e.g., a bead, a sheet, a well, and the like.

Metal ions metal ions can be divided into three categories (hard, intermediate and soft) based on their preferential reactivity towards nucleophiles. To the group of hard metal ions belong $Fe^{3+}$, $Ca^{2+}$ and $Al^{3+}$ which show a preference for oxygen. Soft metal ions such as $Cu^+$, $Hg^{2+}$, $Ag^+$, etc, prefer sulfur. Intermediate metal ions ($Cu^{2+}$, $Ni^{2+}$, $Zn^{2+}$, $Co^{2+}$) coordinate nitrogen, oxygen and sulfur. Histidine residues bind intermediate metal ions with high affinity. The binding constant of an average protein with a single histidyl residue is about $4.5 \times 10^3 M^{-1}$.

In some embodiments, a metal ion chelate resin is a $Co^{2+}$-immobilizing resin. Such resins are described in U.S. Pat. No. 5,962,641, the contents of which are incorporated herein by reference.

In some embodiments, the invention provides methods of purifying a subject fusion protein using multiple metal ion affinity resins, e.g., two or more different metal ion affinity resins. The multiple metal ion affinity resins can be provided in the same column, e.g., mixed together, or layered one on top of the other; or provided in two separate, tandem columns. In some embodiments, a first metal ion affinity resin comprises a matrix, a first metal ion chelating ligand, and a first immobilized metal ion, wherein the first metal ion is selected from the group consisting of $Fe^{3+}$, $Ca^{2+}$ and $Al^{3+}$; and a second metal ion affinity resin comprises a matrix, a second metal ion chelating ligand, and a second immobilized metal ion, wherein the second immobilized metal ion is selected from the group consisting of $Cu^{2+}$, $Ni^{2+}$, $Zn^{2+}$, $Co^{2+}$. In other embodiments, a first metal ion affinity resin comprises a matrix, a metal ion chelating ligand, and a first immobilized metal ion, wherein the first metal ion is selected from the group consisting of $Fe^{3+}$, $Ca^{2+}$ and $Al^{3+}$; and a second metal ion affinity resin comprises a matrix, a metal ion chelating ligand, and a second immobilized metal ion, wherein the second immobilized metal ion is selected from the group consisting of $Cu^{2+}$, $Ni^{2+}$, $Zn^{2+}$, $Co^{2+}$. In these embodiments, the first and second metal ion affinity resins comprise the same metal ion ligand. In some embodiments, a sample comprising a fusion protein is applied to a first resin, the resin washed to remove unbound components of the sample, bound fusion protein eluted from the first resin, and the eluted fusion protein applied to the second resin, followed by washing and eluting steps.

Conditions for Binding

The conditions under which a protein sample comprising a subject fusion protein is applied to a metal ion affinity resin will vary according to various parameters, including the inherent properties of the fusion protein, the properties of the undesired components of the protein sample, etc. Generally, the sample is applied to the metal ion affinity resin, and the resin is equilibrated with a solution. "Conditions for binding" include a condition of the sample being applied, as well as any equilibration conditions. Those skilled in the art can readily determine appropriate conditions for binding of a fusion protein in a sample to a metal ion affinity resin, based on known and determined properties of the fusion protein, etc. Conditions may be chosen such that a fusion protein retains its native conformation and/or activity. For example, a fusion protein comprising a polypeptide derived from an extreme halophile may be contacted with a metal ion affinity resin under high salt (e.g., 1.5 to 3 M NaCl). Salt concentrations suitable for applying a sample comprising a subject fusion protein to a metal ion affinity resin range from about 0.01 M NaCl to about 3 M NaCl, from about 0.05 M NaCl to about 1.5 M NaCl, from about 0.1 M NaCl to about 1.0 M NaCl, or from about 0.2 M NaCl to about 0.5 M NaCl. The pH conditions suitable for applying a sample comprising a subject fusion protein to a metal ion affinity resin range from about 3.5 to about 11, from about 4.0 to about 10.0, from about 4.5 to about 9.5, from about 5.0 to about 9.0, from about 5.5 to about 8.5, from about 6.0 to about 8.0, or from about 6.5 to about 7.5. Temperature conditions suitable for applying a sample comprising a subject fusion protein to a metal ion affinity resin range from about 15° C. to about 40° C., from about 20° C. to about 37° C., or from about 22° C. to about 25° C. Various additional substances may be included, including, but not limited to, detergents (e.g., sodium dodecyl sulfate, e.g., from about 0.05% to about 2%); non-ionic detergents, e.g., Tween 20™, and the like; chaotropic agents and denaturants, e.g., urea, and guanidinium HCl; buffers, e.g., Tris-based buffers, borate—based buffers, phosphate-based buffers, imidazole, HEPES, PIPES, MOPS, PIPES, TES, and the like.

Purification Steps

In some embodiments, the invention provides a method of purifying a fusion protein from a sample comprising the fusion protein, comprising contacting a sample comprising the fusion protein with an immobilized metal ion affinity resin under conditions which favor binding of the fusion protein to the immobilized metal ion, thereby immobilizing the fusion protein; and eluting the immobilized fusion protein.

In other embodiments, the methods comprise contacting a sample comprising a fusion protein with a first immobilized metal ion affinity resin comprising a first immobilized metal ion and a second immobilized metal ion affinity resin comprising a second immobilized metal ion, wherein the fusion protein comprises a fusion partner polypeptide and a metal ion affinity peptide, and wherein the affinity peptide has a first affinity to a first immobilized metal ion and a second affinity to a second immobilized metal ion. In these embodiments, multiple resins, as described above, are used. The first affinity is generally at least about 50%, at least about 100% (or 2-fold), at least about 4-fold, at least about 5-fold, at least about 7-fold, at least about 10-fold, at least about 20-fold, at least about 50-fold, or at least about 100-fold, or more, higher than the second affinity.

In one non-limiting example, in a purification scheme utilizing two different immobilized metal ions, a sample including a subject fusion protein is applied to a first column containing a first resin with a first immobilized metal ion under conditions that favor binding of the fusion protein to the first immobilized metal ion. The first column is washed to remove any unbound components of the sample. The bound fusion protein is eluted, then applied to a second column containing a second resin with a second immobilized metal ion under conditions that favor binding of the fusion protein to the second immobilized metal ion. The second column is washed to remove any unbound components, and the bound fusion protein is eluted.

Washing

One or more washing steps may be included, to remove undesired components. A washing step may be performed after a fusion protein is immobilized on a resin. The composition and temperature of a washing solution may vary according to the desired result. The optimal composition and temperature of a washing solution can readily be determined by those skilled in the art, based on known properties of the immobilized fusion protein. Wash solutions may comprise a buffer, and may further comprise additional components, as necessary, including, but not limited to, a detergent.

Eluting

The immobilized fusion protein can be eluted using a pH gradient; addition of a competitor, e.g., an organic acid, phosphates; addition of a displacer such as imidazole; and the like.

Utilyty

The subject methods find use in a number of different applications where protein purification is desired.

Metal ion affinity peptide-tagged recombinant proteins are useful for the study of protein-protein interactions and nucleic acid molecule-protein interactions, using solid phase IMAC having bound thereto a subject fusion protein. In these applications, the solid phase IMAC serves to anchor a subject fusion protein, thereby immobilizing the subject fusion protein. Analysis of protein-protein interactions and nucleic acid molecule-protein interactions are generally carried out by detecting a protein or nucleic acid molecule bound to the fusion partner polypeptide of an immobilized subject fusion protein. Detection can be carried out using any known method, and in many instances involves use of a detectably labeled reagent, e.g., a detectably labeled antibody specific for a given protein, a detectably labeled nucleic acid molecule that hybridizes to a nucleic acid molecule to be detected, and the like.

Also contemplated is the use of the subject methods in high throughput systems, e.g., where protein purification of a large number of samples is desired. High throughput systems find use, e.g., in massive parallel gene expression experiments, e.g., to determine the effect of an agent on synthesis of a protein or set of proteins; to analyze developmental stage-specific, or tissue-specific synthesis of a protein; to analyze the phosphorylation state of a protein; and the like.

The methods are useful in applications to characterize a protein of unknown identity or function. For example, a putative coding region identified in a sequencing project is cloned into an expression vector such that the encoded protein comprises a subject metal ion affinity peptide, the vector is introduced into a host cell for transcription and translation of the putative coding region, and the protein purified, as described in more detail below. The function of the protein can then be determined, using any known assay method, including, but not limited to, assays for protein-protein interaction; assays for protein-nucleic acid molecule interactions; assays for enzymatic activity; and the like.

The methods are further useful in carrying out enzymatic reactions. A subject fusion protein having as a fusion partner a protein with enzymatic activity is immobilized on an IMAC solid support, and contacting the immobilized enzyme with a substrate under conditions appropriate to the enzymatic activity of the enzyme. In general, the immobilized enzyme is purified using a method as described herein before contacting the enzyme with a substrate. The product(s) of the enzymatic reaction, which are in the medium (e.g., the buffer in which the enzymatic reaction took place), are readily collected by separating the medium from the IMAC solid support. Separation of the medium from the IMAC solid support is achieved using standard methods, e.g., using standard techniques of column chromatography, centrifugation, and the like.

Kits

The invention provides kits for practicing the subject methods. Thus, the invention provides a kit for purification of a fusion protein comprising a metal ion affinity peptide.

In some embodiments, a kit of the invention comprises a recombinant vector of the invention. In some embodiments, a kit further comprises an appropriate restriction enzyme(s), ligases, and other reagents for inserting a heterologous nucleic acid molecule into the recombinant vector. The kit may further comprise bacteria; reagents for introducing the recombinant vector into the bacteria; reagents for selecting bacteria that comprise the recombinant vector; reagents for inducing expression of the fusion protein; and reagents for disrupting bacteria after a fusion protein is produced.

In other embodiments, a kit comprises a metal ion affinity resin, an extraction buffer, a wash buffer, and an elution buffer. In some of these embodiments, a kit further comprises a column for use in protein purification. In other embodiments, the metal ion affinity resin is provided attached to a solid support.

In other embodiments, a kit comprises, in addition to a recombinant vector, and optionally other components as described above, one or more metal ion affinity resins. In some of these embodiments, a kit further comprises, extraction, wash, and elution buffers, and, in some embodiments, further comprises one or more columns.

The kit may optionally provide additional components that are useful in the procedure, including, but not limited to, buffers, developing reagents, labels, reacting surfaces, means for detections, control samples, standards, instructions, and interpretive information.

Finally, in many embodiments of the subject kits, the kits will further include instructions for practicing the subject methods or means for obtaining the same (e.g., a website URL directing the user to a webpage which provides the instructions), where these instructions are typically printed on a substrate, which substrate may be one or more of: a package insert, the packaging, reagent containers and the like.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Construction of Vectors and Expression of Fusion Protein

A DNA sequence corresponding to the affinity peptide of the present invention is fused to the DNA coding sequence of a protein of interest. The polynucleotide sequence for the affinity peptide is fused most generally at or close to the DNA sequence coding for the N- or C-terminal amino acid of the protein of interest. This results in a DNA sequence which codes for a fusion protein comprising the affinity peptide and the protein of interest.

In addition, a polynucleotide sequence that codes for a protein proteolytic site is incorporated into the fusion protein DNA sequence between the sequence for the affinity peptide and the sequence of the protein of interest. This type of DNA construct results in a fusion protein product which has a proteolytic site. This site allows for the eventual regeneration of the protein of interest from the fusion protein by limited proteolysis and a second chromatography step. The second chromatography step, in which the product of the proteolysis is loaded onto an immobilized metal ion affinity column, results in the separation of the protein of interest from the affinity peptide.

An additional embodiment of the present invention provides a DNA sequence coding for a polypeptide "secretion signal" introduced into the DNA that codes for the fusion protein. This secretion signal, when expressed, causes the fusion protein to be secreted into the culture media after the fusion protein is synthesized in the cell. Since a large number of cellular proteins are not transported out of the cell, isolation and purification of the fusion protein is enhanced as the requirements for cell disruption, extraction and removal of unwanted cell components are eliminated.

FIG. 1 illustrates the pHAT-EK vector containing the cDNA of recombinant enterokinase (EK cDNA) fused to an affinity purification peptide. FIG. 2 provides the DNA and amino acid sequence of the pHAT-EK vector shown in FIG. 1. FIG. 3 shows various DNA and amino acid sequence variants of the affinity purification site of the present invention.

Example 2

Purification of Fusion Protein on $Co^{2+}$-TALON Agarose

An IMAC column was prepared in the following manner: Approximately 2.75 mL of $Co^{2+}$-TALON Superflow 6 (Amersham, Pharmacia) was transferred to a vacuum bottle, diluted with the same volume of deionized water and degassed under vacuum for 10 minutes. The gel suspension was poured into a column (3×1 cm. i.d.) trapped on the bottom with a degassed adapter and left to settle. The column was filled to the top with degassed deionized water, and a top adapter was gently pushed down toward the column bed until there was no space between the top surface of the gel and the adapter. The column was washed with 3 column volumes of deionized water at a flow rate of 0.5 mL per min.

Purification of the fusion protein on $CO^{2+}$-TALON Superflow 6 was carried out by first equilibrating the IMAC column with 5 to 10 column volumes of the equilibration buffer. The sample was then loaded on the IMAC column at a flow rate of 1.0 mL per min, and 1 mL fractions were collected. The column was washed with the equilibration buffer until a baseline was reached (absorbance of the fractions at 280 nm as less than 2 mAU higher than the absorbance of the equilibration buffer).

The adsorbed material was eluted with elution buffer (20 mM sodium phosphate buffer containing 1.0 M sodium chloride and 0.15 M imidazole pH 7.0) and absorbance at 280 nm was determined on a spectrophotometer. Protein content of each fraction was determined as described in M. Bradford, *Analytical Biochemistry*, 72 (1976) 248.

Example 3

Isolation and Purification of Fusion Protein Consisting of Affinity Peptide and Green Fluorescent Protein UV Mutant (GFPuv)

An affinity peptide/GFP fusion protein was isolated from *E coli* cells which had been transformed with the pHAT-GFPuv vector (FIG. 6). Cell paste (0.39 g) was transferred to pre-cooled mortar, 1.2 g of alumina was added, and the mixture was ground for 2 minutes. Extraction buffer (5 mL, stored at 4° C.) was added, and, after additional grinding for 2 minutes, the mixture was transferred into four eppendorph tubes. The suspension was added to the eppendorph tubes and centrifuged for 12 minutes at 12,000 rpm (11,750 ×g). The clear supernatant (approximately 6 mL) was used as a starting sample for IMAC.

The extraction and chromatography equilibration buffers consisted of 20 mM sodium phosphate buffer containing 1.0 M sodium chloride and 5 mM imidazole pH 7.0 (1 L). The elution buffer for IMAC consisted of 20 mM sodium phosphate buffer containing 1.0, M sodium chloride and 150 mM imidazole pH 7.0 (0.2 L).

The IMAC was carried out in the following manner: Approximately 2.75 mL of $Co^{2+}$-TALON Superflow 6 (Amersham, Pharmacia) was transferred to a vacuum bottle, diluted with the same volume of deionized water and degassed under vacuum for 10 minutes. The gel suspension was poured into a column (3×1 cm. i.d.) trapped on the bottom with a degassed adapter and left to settle. The column was filled to the top with degassed deionized water, and top adapter was gently pushed down toward the column bed until there was no space between the top surface of the gel and the adapter. The column was washed with 3 column volumes of deionized water at a flow rate of 0.5 mL per mm.

Purification of the fusion protein on $Co^{2+}$-TALON Superflow 6 was carried out by first equilibrating the IMAC column with 5 to 10 column volumes of the equilibration buffer. The sample was the loaded on the IMAC column at a flow rate of 1.0 mL per min, and 1 mL fractions were collected. The column was washed with the equilibration buffer until a baseline was reached (absorbance of the fractions at 280 nm as less than 2 mAU higher than the absorbance of the equilibration buffer). The adsorbed material was then eluted with elution buffer.

Absorbance of each fraction at 280 nm was determined on a spectrophotometer;

and protein content of each fraction also was determined as described in M. Bradford, *Analytical Biochemistry*, 72 (1976) 248. Fluorescence of each fraction was determined on a microplate reader, and the purity of the fusion protein was determined also by SDS-electrophoresis. Results show that more than 95% of the fusion protein was recovered in the fractions obtained.

It is evident from the above results and discussion that the invention provides metal ion affinity peptides, fusion proteins thereof, and methods of purifying same, which provide for improved purification of proteins.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated polynucleotide comprising a nucleotide sequence that encodes a metal ion affinity peptide having a formula of $NH_2$-(His-Asn)$_n$ or (His-Asn)$_n$-COOH, where n=6 (SEQ ID NO: 15).

2. The polynucleotide according to claim 1 wherein the polynucleotide comprises a nucleotide sequence encoding a fusion protein comprising a polypeptide and the metal ion affinity peptide, wherein the metal ion affinity peptide is fused to an amino- or carboxy-terminal amino acid of the polypeptide.

3. A recombinant vector comprising the polynucleotide according to claim 1.

4. A recombinant host cell comprising the recombinant vector according to claim 3.

5. The recombinant host cell according to claim 4, wherein said cell is a prokaryotic cell.

6. The recombinant host cell according to claim 4, wherein said cell is a eukaryotic cell.

7. A kit for purifying a protein, comprising:
a) the recombinant vector according to claim 3; and
b) a metal ion affinity resin.

8. The kit according to claim 7, further comprising:
an extraction buffer;
a wash buffer; and
an elution buffer.

9. The kit according to claim 8, further comprising a column.

10. An isolated polynucleotide comprising a nucleotide sequence that encodes a metal ion affinity peptide having a formula of $NH_2$-(His-Asn)$_n$ or (His-Asn)$_n$-COOH, where n=3–5 (SEQ ID NOs: 27–29) or 7–10(SEQ ID NOs:30–33).

11. The polynucleotide according to claim 10, wherein the polynucleotide comprises a nucleotide sequence encoding a fusion protein comprising a polypeptide and the metal ion affinity peptide, wherein the metal ion affinity peptide is fused to an amino- or carboxy-terminal amino acid of the polypeptide.

12. A recombinant vector comprising the polynucleotide according to claim 10.

13. A recombinant host cell comprising the recombinant vector according to claim 12.

14. The recombinant host cell according to claim 13, wherein said cell is a prokaryotic cell.

15. The recombinant host cell according to claim 13, wherein said cell is a eukaryotic cell.

16. A kit for purifying a protein, comprising:
a) the recombinant vector according to claim 12; and
b) a metal ion affinity resin.

17. The kit according to claim 16, further comprising:
an extraction buffer;
a wash buffer; and
an elution buffer.

18. The kit according to claim 17, further comprising a column.

* * * * *

UNITED STATES PATENT AND TRADEMARK OFFICE
CERTIFICATE OF CORRECTION

| | |
|---|---|
| PATENT NO. | : 7,176,298 B2 |
| APPLICATION NO. | : 09/858332 |
| DATED | : February 13, 2007 |
| INVENTOR(S) | : Grigoriy Simeonov Tchaga et al. |

It is certified that error appears in the above-identified patent and that said Letters Patent is hereby corrected as shown below:

Column 41, Line 38, please change as follows: claim 4[[.]] to: claim 4

Signed and Sealed this

Twenty-second Day of May, 2007

JON W. DUDAS
*Director of the United States Patent and Trademark Office*

UNITED STATES PATENT AND TRADEMARK OFFICE
CERTIFICATE OF CORRECTION

PATENT NO.         : 7,176,298 B2
APPLICATION NO. : 09/858332
DATED              : February 13, 2007
INVENTOR(S)        : Grigoriy Simeonov Tchaga et al.

It is certified that error appears in the above-identified patent and that said Letters Patent is hereby corrected as shown below:

Column 41, Line 38, please change as follows: claim 4"." to: --claim 4--

Signed and Sealed this

Twelfth Day of June, 2007

JON W. DUDAS
*Director of the United States Patent and Trademark Office*